US011186635B2

(12) United States Patent
Bensussan et al.

(10) Patent No.: US 11,186,635 B2
(45) Date of Patent: Nov. 30, 2021

(54) MONOCLONAL ANTIBODIES BINDING TO THE CD160 TRANSMEMBRANE ISOFORM

(71) Applicants: INSERM (INSTITUT NATIONAL DE LA SANTÉ ET DE LA RECHERCHE MÉDICALE), Paris (FR); UNIVERSITÉ PARIS DIDEROT—PARIS 7, Paris (FR); UNIVERSITÉ DE MONTPELLIER, Montpellier (FR); INSTITUT JEAN GODINOT, Reims (FR); INSTITUT RÉGIONAL DU CANCER DE MONTPELLIER, Montpellier (FR)

(72) Inventors: Armand Bensussan, Paris (FR); Bruno Robert, Montpellier (FR); Pierre Martineau, Montpellier (FR); Myriam Chentouf, Montpellier (FR); Anne Marie-Cardine, Paris (FR); Jérôme Giustiniani, Reims (FR)

(73) Assignees: INSTITUT NATIONAL DE LA SANTÉ ET DE LA RECHERCHÉ MÉDICAL (INSERM); UNIVERSITÉ DE PARIS; UNIVERSITÉ DE MONTPELLIER; INSTITUT JEAN GODINOT; INSTITUT RÉGIONAL DU CANCER DE MONTIPELLIER

( * ) Notice: Subject to any disclaimer, the term of this patent is extended or adjusted under 35 U.S.C. 154(b) by 0 days.

(21) Appl. No.: 16/343,889

(22) PCT Filed: Oct. 25, 2017

(86) PCT No.: PCT/EP2017/077261
§ 371 (c)(1),
(2) Date: Apr. 22, 2019

(87) PCT Pub. No.: WO2018/077926
PCT Pub. Date: May 3, 2018

(65) Prior Publication Data
US 2019/0256595 A1    Aug. 22, 2019

(30) Foreign Application Priority Data

Oct. 25, 2016 (EP) .................................... 16306392

(51) Int. Cl.
*C07K 16/28* (2006.01)
*A61K 47/68* (2017.01)
*A61P 35/00* (2006.01)

(52) U.S. Cl.
CPC ...... *C07K 16/2803* (2013.01); *A61K 47/6801* (2017.08); *A61K 47/6819* (2017.08); *C07K 2317/21* (2013.01); *C07K 2317/33* (2013.01); *C07K 2317/34* (2013.01)

(58) Field of Classification Search
CPC ............ C07K 16/2803; C07K 2317/33; C07K 2317/21; C07K 2317/34; C07K 2317/56; C07K 2317/54; C07K 2317/55; C07K 2317/565; C07K 2317/622; C07K 16/2896; C07K 2319/33; A61K 47/6801; A61K 2039/505; A61K 39/39533; A61K 47/6819; A61P 7/06; A61P 7/00; A61P 37/06; A61P 35/02; A61P 35/00; A61P 31/00
See application file for complete search history.

(56) References Cited

U.S. PATENT DOCUMENTS

| | | | |
|---|---|---|---|
| 4,816,567 | A | 3/1989 | Shmuel et al. |
| 4,861,719 | A | 8/1989 | Dusty |
| 5,278,056 | A | 1/1994 | Arthur et al. |
| 5,500,362 | A | 3/1996 | Robinson et al. |
| 5,635,483 | A | 6/1997 | Pettit et al. |
| 5,663,149 | A | 9/1997 | Pettit et al. |
| 5,714,350 | A | 2/1998 | Sung et al. |
| 5,780,588 | A | 7/1998 | Pettit et al. |
| 5,821,337 | A | 10/1998 | Carter et al. |
| 5,882,877 | A | 3/1999 | Gregory et al. |
| 6,013,516 | A | 1/2000 | Inder et al. |
| 6,194,551 | B1 | 2/2001 | Ekinaduese et al. |
| 6,214,345 | B1 | 4/2001 | Firestone et al. |
| 6,350,861 | B1 | 2/2002 | Sung et al. |
| 6,703,199 | B1 | 3/2004 | Shohei |
| 2003/0153043 | A1 | 8/2003 | Carr et al. |

(Continued)

FOREIGN PATENT DOCUMENTS

| | | |
|---|---|---|
| EP | 0404097 A2 | 12/1990 |
| EP | 1176195 B1 | 1/2002 |
| EP | 1297172 B1 | 11/2005 |

(Continued)

OTHER PUBLICATIONS

Lloyd et al., Protein Engineering, Design & Selection 22:159-168 (Year: 2009).*

(Continued)

*Primary Examiner* — Phuong Huynh

(74) *Attorney, Agent, or Firm* — James H. Velema, Esq.; Judith L. Stone-Hulslander

(57) ABSTRACT

The present invention relates to monoclonal antibodies that bind to the CD160-TM isoform. The inventors developed new monoclonal antibodies which bind to the CD160-TM isoform but dot not bind to the CD160 GPI-anchored isoform not to the CD160 soluble isoform. In particular, the antibodies of the present invention are suitable for amplifying NK cell activation and therefore cytotoxic functions NK cells.

14 Claims, 7 Drawing Sheets

Figure 1:
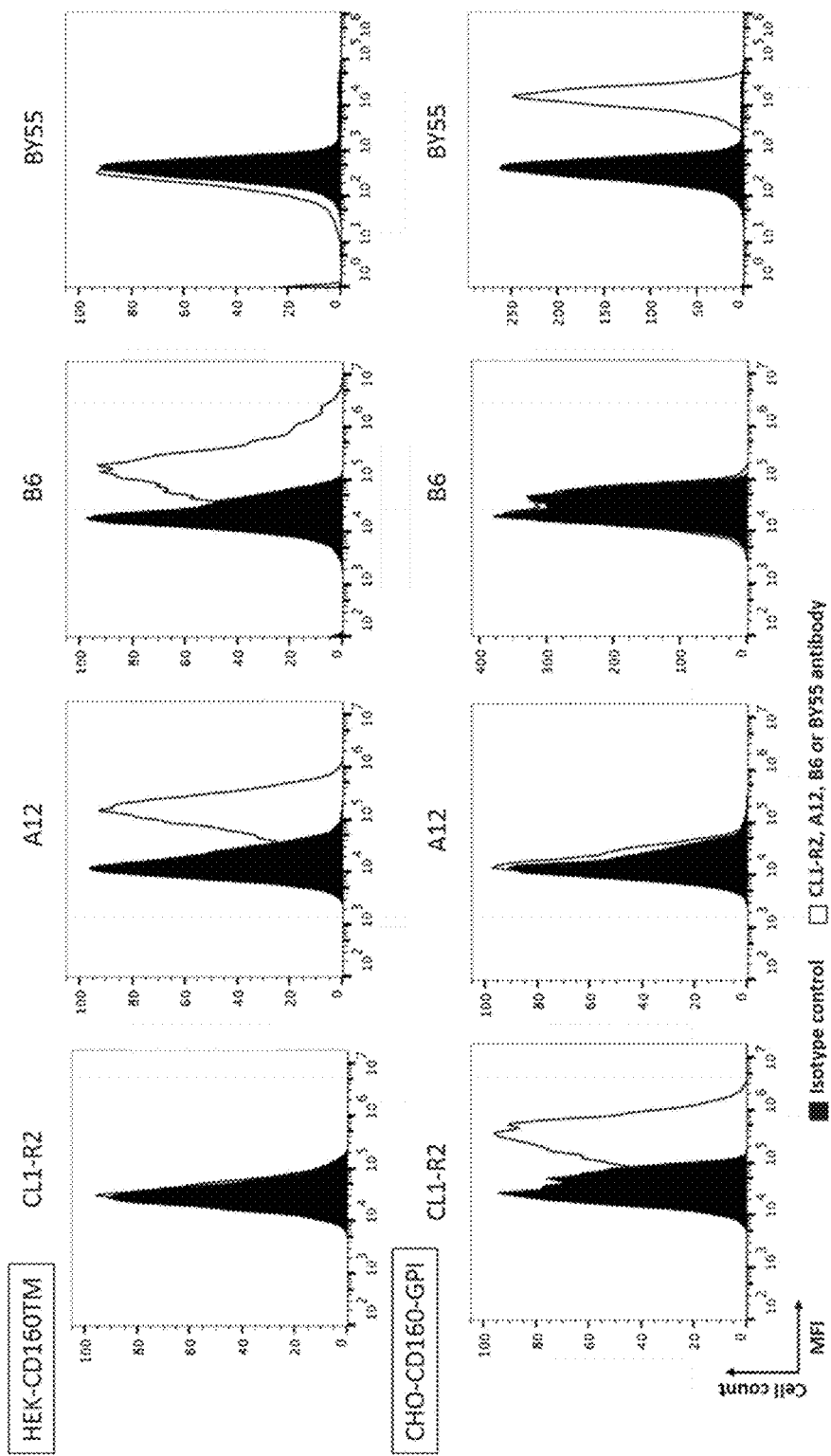

Specification includes a Sequence Listing.

(56) References Cited

U.S. PATENT DOCUMENTS

| | | | | |
|---|---|---|---|---|
| 2013/0045871 A1* | 2/2013 | DeLisa | ............. | C12N 15/1037 506/1 |
| 2014/0328753 A1* | 11/2014 | Clofent-Sanchez | ... | C07K 16/18 424/1.49 |

FOREIGN PATENT DOCUMENTS

| | | |
|---|---|---|
| WO | 8912624 A2 | 12/1989 |
| WO | 9311161 A1 | 6/1993 |
| WO | 9419478 A1 | 9/1994 |
| WO | 9514785 A1 | 6/1995 |
| WO | 9622378 A1 | 7/1996 |
| WO | 9954342 A1 | 10/1999 |
| WO | 02088172 A2 | 11/2002 |
| WO | 03026577 A2 | 4/2003 |
| WO | 03035835 A2 | 5/2003 |
| WO | 200348731 A2 | 6/2003 |
| WO | 2004010957 A2 | 2/2004 |
| WO | 2005081711 A2 | 9/2005 |
| WO | 2005082023 A2 | 9/2005 |
| WO | 2005084390 A2 | 9/2005 |
| WO | 2006015886 A1 | 2/2006 |
| WO | 2006132670 A2 | 12/2006 |
| WO | 200700860 A1 | 1/2007 |
| WO | 2007011968 A2 | 1/2007 |
| WO | 2008009711 A2 | 1/2008 |
| WO | 2008155363 A2 | 12/2008 |
| WO | 2012059882 A2 | 5/2012 |
| WO | 2016113351 A1 | 7/2016 |

OTHER PUBLICATIONS

Edwards et al., J Mol Biol 334(1): 103-118 (Year: 2003).*
Roitt et al., in Immunology second edition, Gower Medical Publishing New York , p. 5.8 to 5.9 (Year: 1989).*
Rudikoff et al., Proc Natl Acad Sci USA 79: 1979 (Year: 1982).*
Barrios et al., J Molecular Recognition 17: 332-338 (Year: 2004).*
MacCallum et al., J Mol. Biol. 262: 732-745 (Year: 1996).*
Wu et al., J. Mol. Biol. 294: 151-162 (Year: 1999).*
Dermer et al., Bio/Technology, vol. 12 p. 320 (Year: 1994).*
Giustiniani et al., "Identification and characterization of a transmembrane isoform of CD160 (CD160-TM), a unique activating receptor selectively expressed upon human NK cell activation", Journal of Immunology, Jan. 2009, vol. 182, No. 1, pp. 63-71.
Giustiniani et al., "Possible pathogenic role of the transmembrane isoform of CD160 NK lymphocyte receptor in paroxysmal nocturnal hemoglobinuria", Current Molecular Medicine, Feb. 2012, vol. 12, No. 2, pp. 188-198.
Batzer et al., "Amplification dynamics of human-specific (HS) Alu family members", Nucleic Acids Research, Jul. 1991, vol. 19, No. 13, pp. 3619-3623.
Ohtsuka et al., "An alternative approach to deoxyoligonucleotides as hybridization probes by insertion of deoxyinosine at ambiguous codon positions", Journal of Biological Chemistry, Mar. 1985, vol. 260, No. 5, pp. 2605-2608.
Rossolini et al., "Use of deoxyinosine-containing primers vs degenerate primers for polymerase chain reaction based on ambiguous sequence information", Molecular and Cellular Probes, Apr. 1994, vol. 8, No. 2, pp. 91-98.
Holliger et al., ""Diabodies": small bivalent and bispecific antibody fragments", Proceedings of the National Academy of Sciences USA, Jul. 1993, vol. 90, No. 14, pp. 6444-6448.
Holliger and Hudson, "Engineered antibody fragments and the rise of single domains", Nature Biotechnology, Sep. 2005, vol. 23, No. 9, pp. 1126-1136.
Leong et al., "Adapting pharmacokinetic properties of a humanized anti-interleukin-8 antibody for therapeutic applications using site-specific pegylation". Cytokine, Nov. 2001, vol. 16, No. 3, pp. 106-119.
Delgado et al., "Enhanced tumour specificity of an anti-carcinoembrionic antigen Fab' fragment by poly(ethylene glycol) (PEG) modification", British Journal of Cancer, Jan. 1996, vol. 73, No. 2, pp. 175-182.
Anumanthan et al., "Cloning of BY55, a novel Ig superfamily member expressed on NK cells, CTL, and intestinal intraepithelial lymphocytes", Journal of Immunology, Sep. 1998, vol. 161, No. 6, pp. 2780-2790.
Maiza et al., "A novel 80-kD cell surface structure identifies human circulating lymphocytes with natural killer activity", Journal of Experimental Medicine, Sep. 1993, vol. 178, No. 3, pp. 1121-1126.
Nikolova et al., "BY55/CD160 acts as a co-receptor in TCR signal transduction of a human circulating cytotoxic effector T lymphocyte subset lacking CD28 expression", International Immunology, May 2002, vol. 14, No. 5, pp. 445-451.
Giustiniani et al., "A soluble form of the MHC class I-specific CD160 receptor is released from human activated NK lymphocytes and inhibits cell-mediated cytotoxicity", Journal of Immunology, Feb. 2007, vol. 178, No. 3, pp. 1293-1300.
Scathchard, "The attraction of proteins for small molecules and ions", Annals of the New York Academy of Sciences USA, May 1949, vol. 51, p. 660.
Kohler and Milstein, "Continuous cultures of fused cells secreting antibody of predefined specificity", Nature, Aug. 1975, vol. 256, No. 5517, pp. 495-497.
Clackson et al., "Making antibody fragments using phage display libraries", Nature, Aug. 1991, vol. 352, No. 6336, pp. 624-628.
Marks et al., "By-passing immunization. Human antibodies from V-gene libraries displayed on phage", Journal of Molecular Biology, Dec. 1991, vol. 222, No. 3, pp. 581-597.
Jones et al., "Replacing the complementarity-determining regions in a human antibody with those from a mouse", Nature, May-Jun. 1986, vol. 321, No. 6069, pp. 522-525.
Riechmann et al., "Reshaping human antibodies for therapy", Nature, Mar. 1988, vol. 332, No. 6162, pp. 323-327.
Presta, "Antibody engineering for therapeutics", Current Opinion in Structural Biology, Aug. 2003, vol. 13, No. 4, pp. 519-525.
Morisson et al., "Chimeric human antibody molecules: mouse antigen-binding domains with human constant region domains", Proceedings of the National Academy of Sciences USA, Nov. 1984, vol. 81, No. 21, pp. 6851-6855.
Urlaub and Chasin, "Isolation of Chinese hamster cell mutants deficient in dihydrofolate reductase activity", Proceedings of the National Academy of Sciences USA, Jul. 1980, vol. 77, No. 7, pp. 4216-4220.
Ravetch and Kinet, "Fc receptors", Annual Review of Immunology, 1991, vol. 9, pp. 457-492.
Clynes et al., "Fc receptors are required in passive and active immunity to melanoma", Proceedings of the National Academy of Sciences USA, Jan. 1998, vol. 95, No. 2, pp. 652-656.
Shields, "Lack of fucose on human IgG1 N-linked oligosaccharide improves binding to human Fcgamma RIII and antibody-dependent cellular toxicity", Journal of Biological Chemistry, Jul. 2002, vol. 277, No. 30, p. 26733-26740.
Umana et al., "Engineered glycoforms of an antineuroblastoma IgG1 with optimized antibody-dependent cellular cytotoxic activity", Nature Biotechnology, Feb. 1999, vol. 17, No. 2, pp. 176-180.
Gazzano-Santaro et al., "A non-radioactive complement-dependent cytotoxicity assay for anti-CD20 monoclonal antibody", Journal of Immunological Methods, Mar. 1997, vol. 202, No. 2, pp. 163-171.
Pessino et al., "Molecular Cloning of NKp46: A Novel Member of the Immunoglobulin Superfamily Involved in Triggering of Natural Cytotoxicity", Journal of Experimental Medicine, Sep. 1998, vol. 188, No. 5, pp. 953-960.
Sivori et al., "NKp46 is the major triggering receptor involved in the natural cytotoxicity of fresh or cultured human NK cells. Correlation between surface density of NKp46 and natural cytotoxicity against autologous, allogeneic or xenogeneic target cells", European Journal of Immunology, May 1999, vol. 29, No. 5, pp. 1656-1666.
Brando et al., "Receptors and lytic mediators regulating anti-tumor activity by the leukemic killer T cell line TALL-104", Journal of Leukocyte Biology, Aug. 2005, vol. 78, No. 2, 359-371.

(56) References Cited

OTHER PUBLICATIONS

El-Sherbiny et al., "The Requirement for DNAM-1, NKG2D, and NKp46 in the Natural Killer Cell-Mediated Killing of Myeloma Cells", Cancer Research, Sep. 2007, vol. 67, No. 18, pp. 8444-8449.
Nolte-'T Hoen et al., "Increased surveillance of cells in mitosis by human NK cells suggests a novel strategy for limiting tumor growth and viral replication", Blood, Jan. 2007, vol. 109, No. 2, pp. 670-673.
McNamara et al., Multivalent 4-1BB binding aptamers costimulate CD8+ T cells and inhibit tumor growth in mice, Journal of Clinical Investigation, Jan. 2008, vol. 118, No. 1, pp. 376-386.
Wokye et al., "In vitro activities and postantifungal effects of the potent dolastatin 10 derivative auristatin PHE", Antimicrobial Agents and Chemotherapy, Dec. 2001, vol. 45, No. 12, pp. 3580-3584.
Pettit et al., "Specific Activities of Dolastatin 10 and Peptide Derivatives against Cryptococcus neoformans", Antimicrobial Agents and Chemotherapy, Nov. 1998, vol. 42, No. 11, pp. 2961-2965.
Hartley et al., "SG2285, a novel C2-aryl-substituted pyrrolobenzodiazepine dimer prodrug that cross-links DNA and exerts highly potent antitumor activity", Cancer Research, Sep. 2010, vol. 70, No. 17, pp. 6849-6858.
Howard et al., "Synthesis of a novel C2/C2'-aryl-substituted pyrrolo[2,1-c][1,4]benzodiazepine dimer prodrug with improved water solubility and reduced DNA reaction rate", Bioorganic and Medicinal Chemistry Letters, Nov. 2009, vol. 19, No. 22, pp. 6463-6466.
Sagnou et al., "Design and synthesis of novel pyrrolobenzodiazepine (PBD) prodrugs for ADEPT and GDEPT", Bioorganic and Medicinal Chemistry Letters, Sep. 2000, vol. 10, No. 18, pp. 2083-2086.
Thorpe et al., "The preparation and cytotoxic properties of antibody-toxin conjugates", Immunological Review, 1982, vol. 62, pp. 119-158.
Axup et al., "Synthesis of site-specific antibody-drug conjugates using unnatural amino acids", Proceedings of the National Academy of Sciences USA, Oct. 2012, vol. 109, No. 40, pp. 16101-16106.
Junutula et al., "Engineered thio-trastuzumab-DM1 conjugate with an improved therapeutic index to target human epidermal growth factor receptor 2-positive breast cancer", Clinical Cancer Research, Oct. 2010, vol. 16, No. 19, pp. 4769-4778.
Slootsrta et al., "Structural aspects of antibody-antigen interaction revealed through small random peptide libraries", Molecular Diversity, Feb. 1996, vol. 1, No. 2, pp. 87-96.
Timmerman et al., "Functional reconstruction and synthetic mimicry of a conformational epitope using CLIPS technology", Journal of Molecular Recognition, Sep.-Oct. 2007, vol. 20, No. 5, pp. 283-299.
Bensussan et al., "A novel monoclonal antibody that identified a transmembrane isoform of CD160 (CD160-TM) selectively expressed on human NK cell upon activation", Journal of Immunology, Apr. 2009, vol. 182 (1 Supplement), pp. 90.9.
El-Far et al., "CD160 isoforms and regulation of CD4 and CD8 T-cell responses", Journal of Translational Medicine, Sep. 2014, vol. 12, pp. 217.
International Search Report in PCT Patent Application No. PCT/EP2017/077261 (6 pages).

* cited by examiner

CLUSTAL 2.1 multiple sequence alignment

```
A12VL      QSVLTQPASVSGSPGQSITISCAGTSSDVGGYYGVSWYQQHPGKAPKLMIYDSYRPSGV
B6VL       QSVLTQPASVSGSPGQSITISCAGTSSDVGGYSYVSWYQQHPGKAPKLMIYDSYRPSGV
                                 **         **                   **
                                  CDR1                            CDR2

A12VL      SNRFSGSKSGNTASLTISGLQAEDEADYQCSSSTYYSTRVFGGGTKLEK-
B6VL       SNRFSGSKSGNTASLTISGLQAEDEADYQCSSYTYYSTRVFGGGTKLEIK
                                          **
                                          CDR3
```

CLUSTAL 2.1 multiple sequence alignment

```
A12VH      EVQLVESGGSLVKPGGSLRLSCAASGFTFSNYSMNWVRQAPGKGLEWISYIYGSSRYISY
B6VH       EVQLVESGGSLVKPGGSLRLSCAASGFTFSNYYMNWVRQAPGKGLEWISGIYGSSRYINY
                                                             
                                          CDR1                  CDR2

A12VH      ADFVKGRFTISRDNATNSLYLQMNSLRAEDTAVYYCVR-SYYQGMDVWGRGTLVTVSS
B6VH       ADFVKGRFTISRDNATNSLYLQMNSLRAEDTAVYYCVRSSGYQGMDVWGRGTLVTVSS
                                               
            CDR2                                 CDR3
```

Figure 5

US 11,186,635 B2

MONOCLONAL ANTIBODIES BINDING TO THE CD160 TRANSMEMBRANE ISOFORM

RELATED APPLICATIONS

This application is a 35 U.S.C. § 371 filing of International Patent Application No. PCT/EP2017/077261, filed Oct. 25, 2017, which claims priority to European Patent Application No. 16306392.8, filed Oct. 25, 2016, the entire disclosures of which are hereby incorporated herein by reference in their entirety.

FIELD OF THE INVENTION

The present invention relates to antibodies (preferably monoclonal antibodies) binding to the CD160-TM isoform.

BACKGROUND OF THE INVENTION

CD160 has been initially identified as a GPI-anchored (CD160-GPI) MHC-class I activating receptor mainly expressed on peripheral blood NK cells. It was additionally reported the identification of a CD160 transmembrane isoform (CD160-TM) resulting from the alternative splicing of CD160 gene. It was established that CD160-TM surface expression is highly restricted to NK cells and is activation-dependent (Giustiniani J et al. J Immunol. 2009 Jan. 1; 182(1):63-71). Indeed, CD160-TM is only expressed by activated NK cells, whereas CD160-GPI is expressed by NK cells (activated or not) and by different subsets of T cells. In addition, it was provided evidences that CD160-TM represent a novel activating receptor, as assessed by the increased CD107a NK cell surface mobilization observed upon its engagement (Giustiniani J et al. 2009).

Accordingly, antibodies that bind to the CD160-TM isoform without binding to the CD160 GPI-anchored isoform nor to the CD160 soluble isoform that may result from the proteolytic cleavage of the CD160-GPI isoform can thus be suitable, for example for amplifying NK cell activation and therefore effector functions of NK cells (cytotoxicity, cytokine secretion etc.) or for inducing depletion of CD160-TM expressing cells (in particular activated NK cells) in vivo. In particular, using an antibody capable of binding to the CD160-TM isoform but not to the CD160-GPI isoform will avoid any systemic toxicity such as cytokine storm risk.

WO2008/009711 describes antibody CL1-R2, an IgG1 capable of binding CD160-GPI.

Giustiniani J. et al. (Curr Mol Med. 2012 February; 12(2):188-98.) describes a monoclonal antibody that binds to the CD160-TM isoform. However, this antibody also binds the soluble isoform of CD160.

WO2008/155363 describes the production of polyclonal antibodies directed to CD160-TM but not binding to the CD160-GPI isoform. These antibodies were obtained by immunizing rabbits with a peptide (peptide 2) comprising amino acids 144-158 of CD160-TM (KQRQHLEFSHNNEGTL, SEQ ID NO: 32).

In the present invention, the Inventors developed a novel antibody binding to the CD160-TM isoform, but not to the CD160-GPI or to the soluble CD160 isoforms.

SUMMARY OF THE INVENTION

The present invention relates to human antibodies (preferably monoclonal antibodies) binding to the CD160-TM isoform. In particular, the present invention is defined by the claims.

In particular, the present invention relates to a monoclonal antibody which binds to the extracellular domain of the CD160-TM isoform, wherein said antibody does not bind to the GPI-anchored isoform nor to the CD160 soluble isoform, and wherein the epitope of said monoclonal antibody comprises at least one amino acid residue from amino acid residues 175 to 189 of SEQ ID NO: 1.

In one embodiment, said epitope further comprises at least one amino acid residue from amino acid residues 62 to 85 of SEQ ID NO: 1.

In one embodiment, the monoclonal antibody of the invention is a chimeric antibody, a humanized antibody or a human antibody.

In one embodiment, the monoclonal antibody of the invention comprises a light chain comprising at least one of the following CDR: i) the VL-CDR1 as set forth in SEQ ID NO: 6 wherein $X_{11}$ is Y or S and $X_{12}$ is G or Y, ii) the VL-CDR2 as set forth in SEQ ID NO: 7 and iii) the VL-CDR3 as set forth in SEQ ID NO: 8 wherein $X_3$ is S or Y, and/or a heavy chain comprising at least one of the following CDR i) the VH-CDR1 as set forth in SEQ ID NO: 9 wherein $X_3$ is S or Y, ii) the VH-CDR2 as set forth in SEQ ID NO: 10 wherein $X_1$ is Y or G and $X_{10}$ is N or S and iii) the VH-CDR3 as set forth in SEQ ID NO: 11.

In one embodiment, the monoclonal antibody of the invention comprises a light chain comprising the following CDR: i) the VL-CDR1 as set forth in SEQ ID NO: 6 wherein $X_{11}$ is Y or S and $X_{12}$ is G or Y, ii) the VL-CDR2 as set forth in SEQ ID NO: 7 and iii) the VL-CDR3 as set forth in SEQ ID NO: 8 wherein $X_3$ is S or Y, and a heavy chain comprising the following CDR i) the VH-CDR1 as set forth in SEQ ID NO: 9 wherein $X_3$ is S or Y, ii) the VH-CDR2 as set forth in SEQ ID NO: 10 wherein $X_1$ is Y or G and $X_{10}$ is N or S and iii) the VH-CDR3 as set forth in SEQ ID NO: 11.

In one embodiment, the monoclonal antibody of the invention comprises a light chain comprising the following CDR: i) VL-CDR1: AGTSSDVGGYYGVS (SEQ ID NO: 20), ii) VL-CDR2: YDSYRPS (SEQ ID NO: 7) and iii) VL-CDR3: SSSTYYSTRV (SEQ ID NO: 24), and the heavy chain of the A12 antibody comprises the following CDR i) VH-CDR1: NYSMN (SEQ ID NO: 26), ii) VH-CDR2: YIYGSSRYISYADFVKG (SEQ ID NO: 29) and iii) VH-CDR3: GMDV (SEQ ID NO: 11).

In one embodiment, the monoclonal antibody of the invention comprises a light chain comprising the following CDR: i) VL-CDR1: AGTSSDVGGYSYVS (SEQ ID NO: 23), ii) VL-CDR2: YDSYRPS (SEQ ID NO: 7) and iii) VL-CDR3: SSYTYYSTRV (SEQ ID NO: 25), and the heavy chain of the A12 antibody comprises the following CDR i) VH-CDR1: NYYMN (SEQ ID NO: 27), ii) VH-CDR2: GIYGSSRYINYADFVKG (SEQ ID NO: 30) and iii) VH-CDR3: GMDV (SEQ ID NO: 11).

In one embodiment, the monoclonal antibody of the invention comprises a heavy chain having at least 70% of identity with SEQ ID NO: 12 or SEQ ID NO: 14 and a light chain having at least 70% of identity with SEQ ID NO: 13 or SEQ ID NO: 15. In one embodiment, the monoclonal antibody of the invention comprises a heavy chain identical to SEQ ID NO: 12 or SEQ ID NO: 14 and a light chain identical to SEQ ID NO: 13 or SEQ ID NO: 15.

In one embodiment, the monoclonal antibody of the invention cross-competes for binding to the CD160-TM isoform with the antibody as described hereinabove.

In one embodiment, the monoclonal antibody of the invention is conjugated to a cytotoxic moiety.

The present invention further relates to a fusion protein comprising a monoclonal antibody as described hereinabove.

The present invention further relates to a nucleic acid molecule which encodes a heavy chain or a light chain of the antibody as described hereinabove. In one embodiment, the nucleic acid molecule of the invention comprises a nucleic acid sequence having 70% of identity with SEQ ID NO: 16, SEQ ID NO: 17, SEQ ID NO: 18 or SEQ ID NO: 19.

The present invention further relates to a host cell which has been transfected, infected or transformed by the nucleic acid as described hereinabove.

In one embodiment, the monoclonal antibody of the invention mediates antibody dependent cellular cytotoxicity, complement dependent cytotoxicity or antibody-dependent phagocytosis.

The present invention further relates to a monoclonal antibody as described hereinabove, for use in a method of treating a cancer wherein cancer cells express CD160-TM, preferably for treating a NK leukemia or a NK lymphoma, such as for example, extranodal and non-extranodal NK/T lymphomas; NK cell derived malignancies; and acute NK leukemia The present invention further relates to a method of depleting a population of cells which express the CD160-TM isoform, a population of malignant NK cells which express the CD160-TM isoform or a population of cells which express the epitope recognized by the A12 or B6 antibody in a subject in need thereof comprising delivering to the subject a therapeutically effective amount of the monoclonal antibody as described hereinabove.

In one embodiment, the monoclonal antibody of the invention does not mediate antibody dependent cellular cytotoxicity, complement dependent cytotoxicity or antibody-dependent phagocytosis.

The present invention further relates to a monoclonal antibody as described hereinabove, for use in a method of treating a cancer, an infectious disease or an autoimmune and/or inflammatory disease.

The present invention further relates to a method of enhancing NK cell activities in a subject in need thereof comprising administering to the subject a therapeutically effective amount of the antibody as described hereinabove.

In one embodiment, the subject suffers from a cancer, an infectious disease or an autoimmune and/or inflammatory disease.

The present invention further relates to a method of enhancing NK cell antibody-dependent cellular cytotoxicity (ADCC) of an antibody in a subject in need thereof comprising administering to the subject the antibody in combination with the monoclonal antibody of the present invention.

The present invention further relates to a method for inhibiting CD160-TM binding to a ligand thereof, comprising contacting CD160-TM with a monoclonal antibody as described hereinabove.

The present invention further relates to a method of treating Paroxysmal Nocturnal Hemoglobinuria in a subject in need thereof comprising administering to the subject a therapeutically effective amount of the monoclonal antibody as described hereinabove, preferably wherein said antibody is a Fab.

The present invention further relates to a pharmaceutical composition comprising the antibody as described hereinabove and a pharmaceutically acceptable carrier.

In the present invention, the following terms have the following meanings:

In the context of the present invention, the following abbreviations for the commonly occurring nucleic acid bases are used. "A" refers to adenine, "C" refers to cytosine, "G" refers to guanine, "T" refers to thymine, and "U" refers to uracil.

The terms "a" and "an" refer to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "nucleic acid" or "polynucleotide" refers to a polymer of nucleotides covalently linked by phosphodiester bonds, such as deoxyribonucleic acids (DNA) or ribonucleic acids (RNA), in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide", "polypeptide", and "protein" are used interchangeably, and refer to a compound comprised of amino acid residues covalently linked by peptide bonds. A polypeptide is not limited to a specific length: it must contain at least two amino acids, and no limitation is placed on the maximum number of amino acids that can comprise a polypeptide's sequence. Peptides, oligopeptides, and proteins are included within the definition of polypeptide, and such terms may be used interchangeably herein unless specifically indicated otherwise. As used herein, the term refers to both short chains, which also commonly are referred to in the art as peptides, oligopeptides and oligomers, for example, and to longer chains, which generally are referred to in the art as proteins, of which there are many types. In one embodiment, as used herein, the term "peptides" refers to a linear polymer of amino acids linked together by peptide bonds, preferably having a chain length of less than about 50 amino acids residues; a "polypeptide" refers to a linear polymer of at least 50 amino acids linked together by peptide bonds; and a protein specifically refers to a functional entity formed of one or more peptides or polypeptides, optionally glycosylated, and optionally of non-polypeptides cofactors. This term also does exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof. Particular polypeptides of interest in the context of this invention are amino acid subsequences comprising CDRs and being capable of binding an antigen.

The term "subject" refers to a warm-blooded animal, preferably a mammal (including humans, domestic and farm animals, and zoo, sports, or pet animals, such as dogs, cats, cattle, horses, sheep, pigs, goats, rabbits, etc . . . ), and more preferably a human. In one embodiment, a subject may be a "patient", i.e., a warm-blooded animal, more preferably a human, who/which is awaiting the receipt of, or is receiving medical care or was/is/will be the object of a medical procedure, or is monitored for the development of a disease. In one embodiment, the subject is an adult (for example a subject above the age of 18). In another embodiment, the subject is a child (for example a subject below the age of 18). In one embodiment, the subject is a male. In another embodiment, the subject is a female.

DETAILED DESCRIPTION OF THE INVENTION

The first object of the present invention relates to an antibody which binds to the CD160-TM isoform but does not bind to the CD160 GPI-anchored isoform.

In one embodiment, the antibody of the invention binds to the extracellular domain of the CD160-TM isoform.

In one embodiment, the antibody of the invention does not bind to the soluble CD160 isoform.

Therefore, in one embodiment, the present invention refers to an antibody that binds to the extracellular domain of the CD160-TM isoform but does not bind to the CD160 GPI-anchored isoform nor the soluble CD160 isoform.

In one embodiment, said antibody is a monoclonal antibody. Therefore, in one embodiment, the present invention refers to a monoclonal antibody that binds to the extracellular domain of the CD160-TM isoform but does not bind to the CD160 GPI-anchored isoform nor the soluble CD160 isoform.

In another embodiment, said antibody is a polyclonal antibody.

As used herein the term "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments (e.g., Fab, Fab', F(ab')$_2$ or scFv . . . ). In natural antibodies, two heavy chains are linked to each other by disulfide bonds and each heavy chain is linked to a light chain by a disulfide bond. There are two types of light chain, lambda (1) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated VL-CDR1, VL-CDR2, VL-CDR3 and VH-CDR1, VH-CDR2, VH-CDR3, respectively. An antigen-binding site, therefore, typically includes six CDRs, comprising the CDR set from each of a heavy and a light chain V region. Framework Regions (FRs) refer to amino acid sequences interposed between CDRs. The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35B (VH-CDR1), residues 50-65 (VH-CDR2) and residues 95-102 (VH-CDR3) according to the Kabat numbering system. The CDRs of the light chain variable domain are located at residues 24-34 (VL-CDR1), residues 50-56 (VL-CDR2) and residues 89-97 (VL-CDR3) according to the Kabat numbering system.

An "intact" antibody is one which comprises an antigen-binding site as well as a CL and at least heavy chain constant domains, CH1, CH2 and CH3. The constant domains may be native sequence constant domains (e.g., human native sequence constant domains) or amino acid sequence variants thereof.

The term "variable" refers to the fact that certain segments of the V domains differ extensively in sequence among antibodies. The V domain mediates antigen binding and defines specificity of a particular antibody for its particular antigen. However, the variability is not evenly distributed across the 110 to 130-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a [beta]-sheet configuration, connected by three hypervariable regions, which form loops connecting, and in some cases forming part of, the [beta]-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The "variable region" or "variable domain" of an antibody refers to the amino-terminal domains of the heavy or light chain of the antibody. The variable domain of the heavy chain may be referred to as "VH". The variable domain of the light chain may be referred to as "VL". These domains are generally the most variable parts of an antibody and contain the antigen-binding sites.

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the VL, and around about 31-35 (H1), 50-65 (H2) and 95-102 (H3) in the VH when numbered in accordance with the Kabat numbering system; Kabat et al., Sequences of Proteins of Immunological Interest, 5th Ed. Public Health Service, National Institutes of Health, Bethesda, Md. (1991)).

In one embodiment, the antibody (preferably the monoclonal antibody) of the present invention is an antibody molecule selected from the group consisting of a whole antibody, a humanized antibody, a single chain antibody, a dimeric single chain antibody, a Fv, a scFv, a Fab, a F(ab)'$_2$, a defucosylated antibody, a bi-specific antibody, a diabody, a triabody, a tetrabody.

In another embodiment, said antibody is an antibody fragment selected from the group consisting of a unibody, a domain antibody, and a nanobody.

In another embodiment, said antibody is an antibody mimetic selected from the group consisting of an affibody, an affilin, an affitin, an adnectin, an atrimer, an evasin, a DARPin, an anticalin, an avimer, a fynomer, a versabody and a duocalin.

"Versabodies" are well known in the art and refer to an antibody mimetic technology. They are small proteins of 3-5 kDa with >15% cysteines, which form a high disulfide density scaffold, replacing the hydrophobic core the typical proteins have.

A "nanobody" is well known in the art and refers to an antibody-derived therapeutic protein that contains the unique structural and functional properties of naturally-occurring heavy chain antibodies. These heavy chain antibodies contain a single variable domain (VHH) and two constant domains (CH2 and CH3). As used herein, the term "derived" indicates a relationship between a first and a second molecule. It generally refers to structural similarity between the first molecule and the second molecule and does not connote or include a process or source limitation on a first molecule that is derived from a second molecule.

The term "diabodies" refers to small antibody fragments prepared by constructing sFv fragments with short linkers (about 5-10 residues) between the VH and VL domains such that inter-chain but not intra-chain pairing of the V domains is achieved, resulting in a bivalent fragment, i.e., fragment having two antigen binding sites. Bispecific diabodies are heterodimers of two "crossover" sFv fragments in which the VH and VL domains of the two antibodies are present on different polypeptide chains. Diabodies are described more fully in, for example, EP 0404097; WO 93/11161; and Holliger et al., Proc. Natl. Acad. Sci. USA, 90:6444-6448 (1993).

An "affibody" is well known in the art and refers to affinity proteins based on a 58 amino acid residue protein domain, derived from one of the IgG binding domain of staphylococcal protein A.

"Anticalins" are well known in the art and refer to an antibody mimetic technology, wherein the binding specificity is derived from lipocalins. Anticalins may also be formatted as dual targeting protein, called Duocalins.

"Avimers" are well known in the art and refer to an antibody mimetic technology.

A "domain antibody" is well known in the art and refers to the smallest functional binding units of antibodies, corresponding to the variable regions of either the heavy or light chains of antibodies.

A "unibody" is well known in the art and refers to an antibody fragment lacking the hinge region of IgG4 antibodies. The deletion of the hinge region results in a molecule that is essentially half the size of traditional IgG4 antibodies and has a univalent binding region rather than the bivalent biding region of IgG4 antibodies.

DARPins (Designed Ankyrin Repeat Proteins) are well known in the art and refer to an antibody mimetic DRP (designed repeat protein) technology developed to exploit the binding abilities of non-antibody polypeptides.

The term "antibody fragment" refers to at least one portion of an intact antibody, preferably the antigen binding region or variable region of the intact antibody, that retains the ability to specifically interact with (e.g., by binding, steric hindrance, stabilizing/destabilizing, spatial distribution) an epitope of an antigen. Examples of antibody fragments include, but are not limited to, Fab, Fab', F(ab')$_2$, Fv fragments, single chain antibody molecules, in particular scFv antibody fragments, disulfide-linked Fvs (sdFv), a Fd fragment consisting of the VH and CH1 domains, linear antibodies, single domain antibodies such as, for example, sdAb (either VL or VH), camelid VHH domains, multi-specific antibodies formed from antibody fragments such as, for example, a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (see U.S. Pat. No. 6,703,199, which describes fibronectin polypeptide minibodies). Papain digestion of antibodies produces two identical antigen-binding fragments, called "Fab" fragments, and a residual "Fc" fragment, a designation reflecting the ability to crystallize readily.

As used herein, a "functional fragment or analog of an antibody" is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, Fc[epsilon]RI.

The "Fc" fragment of an antibody comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

Fragments and derivatives of antibodies of this invention (which are encompassed by the term "antibody" as used in this application, unless otherwise stated or clearly contradicted by context), can be produced by techniques that are known in the art. "Fragments" comprise a portion of the intact antibody, generally the antigen binding site or variable region. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Fragments of the present antibodies can be obtained using standard methods.

For instance, Fab or F(ab')$_2$ fragments may be produced by protease digestion of the isolated antibodies, according to conventional techniques. It will be appreciated that immunoreactive fragments can be modified using known methods, for example to slow clearance in vivo and obtain a more desirable pharmacokinetic profile the fragment may be modified with polyethylene glycol (PEG). Methods for coupling and site-specifically conjugating PEG to a Fab' fragment are described in, for example, Leong et al., Cytokines 16 (3): 106-119 (2001) and Delgado et al., Br. J. Cancer 5 73 (2): 175-182 (1996), the disclosures of which are incorporated herein by reference.

In one embodiment, the antibody (preferably the monoclonal antibody) of the invention is isolated. As used herein, an "isolated antibody" is one that has been separated and/or recovered from a component of its natural environment. Contaminant components of its natural environment are materials that may interfere with diagnostic or therapeutic uses of the antibody, and may include enzymes, hormones, and other proteinaceous or non-proteinaceous components. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity as shown by SDS-PAGE under reducing or non-reducing conditions and using Coomassie blue or, preferably, silver staining. Isolated antibody includes the antibody in situ within recombinant cells since at least one component of the antibody's natural environment will not be present. Ordinarily, however, isolated antibody will be prepared by at least one purification step.

As used herein, the term "CD160" has its general meaning in the art and refers to CD160 molecule. CD160 gene was found to be located on human chromosome 1, and the corresponding protein was originally characterized as a glycosylphosphatidylinositol (GPI)-anchored cell surface molecule. Three CD160 isoforms exist: the CD160-TM isoform, the CD160 GPI-anchored isoform and the soluble CD160 isoform. CD160-GPI is expressed by intestinal intraepithelial T lymphocytes and by a minor subset of circulating lymphocytes including NK cells, TCRγδ and cytotoxic effector CD8$^{bright}$CD28$^-$ T lymphocytes (ANUMANTHAN et al., 1998, J Immunol; 161:2780-2790; MAIZA et al., J. Exp. Med., vol. 178, p: 1121-1126, 1993). The CD160 transmembrane isoform ("CD160-TM") is described in Giustiniani J et al. (J Immunol. 2009 Jan. 1; 182(1):63-71.) as well as in the international patent application WO2008155363 and is characterized by the amino acid sequence as set forth in SEQ ID NO: 1. The extracellular domain of the CD160-TM isoform may be defined by the amino acid sequence ranging from the amino acid residue at position 26 to the amino acid residue at position 189 in SEQ ID NO: 1. The CD160 GPI-anchored isoform ("CD160-GPI") is described in Nikolova M. et al. (Int Immunol. 2002 May; 14(5):445-51.) as well as in the international patent application WO2006015886 and is characterized by the amino acid sequence as set forth in SEQ ID NO: 2 fused to a GPI anchor at the C terminus end. The CD160 soluble isoform is described in Giustiniani J. et al. (J Immunol. 2007 Feb. 1; 178(3):1293-300) and is characterized by the amino acid sequence as set forth in SEQ ID NO: 3. In SEQ ID NO: 1-3, amino acids 1-25 correspond to a signal peptide, and may consequently be absent from the expressed protein.

```
SEQ ID NO: 1: CD160-TM isoform
MLLEPGRGCCALAILLAIVDIQSGGCINITSSASQEGTRLNLICTVWHK

KEEAEGFVVFLCKDRSGDCSPETSLKQLRLKRDPGIDGVGEISSQLMFT

ISQVTPLHSGTYQCCARSQKSGIRLQGHFFSILFTETGNYTVTGLKQRQ

HLEFSHNEGTLSSGFLQEKVWVMLVTSLVALQGMSKRAVSTPSNEGAII

FLPPWLFSRRRRLERMSRGREKCYSSPGYPQESSNQFH

SEQ ID NO: 2 CD160 GPI-anchored isoform
MLLEPGRGCCALAILLAIVDIQSGGCINITSSASQEGTRLNLICTVWHK

KEEAEGFVVFLCKDRSGDCSPETSLKQLRLKRDPGIDGVGEISSQLMFT

ISQVTPLHSGTYQCCARSQKSGIRLQGHFFSILFTETGNYTVTGLKQRQ

HLEFSHNEGTLSS

SEQ ID NO: 3: CD160 soluble isoform
MLLEPGRGCCALAILLAIVDIQSGGCINITSSASQEGTRLNLICTVWHK

KEEAEGFVVFLCKDRSGDCSPETSLKQLRLKRDPGIDGVGEISSQLMFT

ISQVTPLHSGTYQCCARSQKSGIRLQGHFFSILFTETGNYTVTGLKQRQ

HLEFSHNEGTLSS
```

The term "binding" as used herein refers to a direct association between two molecules, due to, for example, covalent, electrostatic, hydrophobic, and ionic and/or hydrogen-bond interactions, including interactions such as salt bridges and water bridges. In particular, as used herein, the term "binding" in the context of the binding of an antibody to a predetermined antigen or epitope typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less. Methods for measuring the $K_D$ of an antibody are well known in the art and include, without limitation, surface plasmon resonance (SPR) technology in a BIAcore 3000 instrument using a soluble form of the antigen as the ligand and the antibody as the analyte. BIACORE® (GE Healthcare, Piscaataway, N.J.) is one of a variety of surface plasmon resonance assay formats that are routinely used to epitope bin panels of monoclonal antibodies. Affinities of antibodies can be readily determined using other conventional techniques, for example, those described by Scatchard et al., (Ann. N.Y. Acad. Sci. USA 51:660 (1949)). Binding properties of an antibody to antigens, cells or tissues may generally be determined and assessed using immunodetection methods including, for example, immunofluorescence-based assays, such as immunohistochemistry (IHC) and/or fluorescence-activated cell sorting (FACS). Typically, an antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ for binding to a non-specific antigen (e.g., BSA, casein), which is not identical or closely related to the predetermined antigen. When the $K_D$ of the antibody is very low (that is, the antibody has a high affinity), then the $K_D$ with which it binds the antigen is typically at least 10,000-fold lower than its $K_D$ for a non-specific antigen. An antibody is said to essentially not bind an antigen or epitope if such binding is either not detectable (using, for example, plasmon resonance (SPR) technology in a BIAcore 3000 instrument using a soluble form of the antigen as the ligand and the antibody as the analyte), or is 100 fold, 500 fold, 1000 fold or more than 1000 fold less than the binding detected by that antibody and an antigen or epitope having a different chemical structure or amino acid sequence.

As used herein, the term "specificity" refers to the ability of an antibody to detectably bind an epitope presented on an antigen, such as a CD160-TM, while having relatively little detectable reactivity with non-CD160-TM proteins such as the CD160 GPI-anchored isoform and the CD160 soluble isoform. Specificity can be relatively determined by binding or competitive binding assays, using, e.g., Biacore instruments, as described elsewhere herein. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules (in this case the specific antigen is a CD160-TM polypeptide). The term "affinity", as used herein, means the strength of the binding of an antibody to an epitope. The affinity of an antibody is given by the dissociation constant Kd, defined as [Ab]×[Ag]/[Ab–Ag], where [Ab–Ag] is the molar concentration of the antibody-antigen complex, [Ab] is the molar concentration of the unbound antibody and [Ag] is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of Biacore instruments.

In one embodiment, the antibody of the invention binds to an epitope comprising at least one amino acid residue from amino acid residues 175 to 189 of SEQ ID NO: 1, or from a sequence sharing at least 60%, 70%, 75%, 80%, 90%, 95%, 96%, 97%, 98%, 99% of identity over amino acid residues 175 to 189 of SEQ ID NO: 1. Amino acid residues 175 to 189 of SEQ ID NO: 1 correspond to the sequence SEQ ID NO: 5 (LVALQGMSKRAVSTP).

As used herein, the term "epitope" refers to a specific arrangement of amino acids located on a protein or proteins to which an antibody binds. Epitopes often consist of a chemically active surface grouping of molecules such as amino acids or sugar side chains, and have specific three dimensional structural characteristics as well as specific charge characteristics. Epitopes can be linear or conformational, i.e., involving two or more sequences of amino acids in various regions of the antigen that may not necessarily be contiguous.

In one embodiment, the antibody of the invention binds to an epitope comprising 1, 2, 3, 4, 5, 6, 7, 8, 9, 10, 11, 12, 13, 14 or 15 amino acid residues from amino acid residues 175 to 189 of SEQ ID NO: 1, or from a sequence sharing at least 60%, 70%, 75%, 80%, 90%, 95%, 96%, 97%, 98%, 99% of identity over amino acid residues 175 to 189 of SEQ ID NO: 1.

In one embodiment, the antibody of the invention binds to an epitope comprising the amino acid sequence as set forth in SEQ ID NO: 5 (LVALQGMSKRAVSTP) or an amino acid sequence sharing at least 60%, 70%, 75%, 80%, 90%, 95%, 96%, 97%, 98%, 99% of identity over SEQ ID NO: 5.

In one embodiment, the antibody of the invention binds to an epitope comprising at least one amino acid residue from amino acid residues 62 to 85 of SEQ ID NO: 1, or from a sequence sharing at least 60%, 70%, 75%, 80%, 90%, 95%, 96%, 97%, 98%, 99% of identity over amino acid residues 62 to 85 of SEQ ID NO: 1. Amino acid residues 62 to 85 of SEQ ID NO: 1 correspond to the sequence SEQ ID NO: 4 (KDRSGDCSPETSLKQLRLKRDPGI).

In one embodiment, the antibody of the invention binds to an epitope comprising 1, 2, 3, 4, 5, 6, 7, 8, 9, 10, 11, 12, 13, 14, 15, 16, 17, 18, 19, 20, 21, 22, 23 or 24 amino acid residues from amino acid residues 62 to 85 of SEQ ID NO: 1, or from a sequence sharing at least 60%, 70%, 75%, 80%, 90%, 95%, 96%, 97%, 98%, 99% of identity over amino acid residues 62 to 85 of SEQ ID NO: 1.

In one embodiment, the antibody of the invention binds to an epitope comprising the amino acid sequence as set forth in SEQ ID NO: 4 (KDRSGDCSPETSLKQLRLKRDPGI) or an amino acid sequence sharing at least 60%, 70%, 75%, 80%, 90%, 95%, 96%, 97%, 98%, 99% of identity over SEQ ID NO: 4.

In one embodiment, the antibody of the invention binds to a conformational epitope.

In one embodiment, the antibody of the invention binds to a conformational epitope comprising:
  at least one amino acid residue from amino acid residues 175 to 189 of SEQ ID NO: 1, or from a sequence sharing at least 60%, 70%, 75%, 80%, 90%, 95%, 96%, 97%, 98%, 99% of identity over amino acid residues 175 to 189 of SEQ ID NO: 1, and
  at least one amino acid residue from amino acid residues 62 to 85 of SEQ ID NO: 1, or from a sequence sharing at least 60%, 70%, 75%, 80%, 90%, 95%, 96%, 97%, 98%, 99% of identity over amino acid residues 62 to 85 of SEQ ID NO: 1.

In one embodiment, the antibody of the invention binds to a conformational epitope comprising:
  1, 2, 3, 4, 5, 6, 7, 8, 9, 10, 11, 12, 13, 14 or 15 amino acid residues from amino acid residues 175 to 189 of SEQ ID NO: 1, or from a sequence sharing at least 60%, 70%, 75%, 80%, 90%, 95%, 96%, 97%, 98%, 99% of identity over amino acid residues 175 to 189 of SEQ ID NO: 1, and
  1, 2, 3, 4, 5, 6, 7, 8, 9, 10, 11, 12, 13, 14, 15, 16, 17, 18, 19, 20, 21, 22, 23 or 24 amino acid residues from amino acid residues 62 to 85 of SEQ ID NO: 1, or from a sequence sharing at least 60%, 70%, 75%, 80%, 90%, 95%, 96%, 97%, 98%, 99% of identity over amino acid residues 62 to 85 of SEQ ID NO: 1.

In one embodiment, the antibody of the invention binds to a conformational epitope comprising:
  the amino acid sequence as set forth in SEQ ID NO: 5 (LVALQGMSKRAVSTP) or an amino acid sequence sharing at least 60%, 70%, 75%, 80%, 90%, 95%, 96%, 97%, 98%, 99% of identity over SEQ ID NO: 5, and
  1, 2, 3, 4, 5, 6, 7, 8, 9, 10, 11, 12, 13, 14, 15, 16, 17, 18, 19, 20, 21, 22, 23 or 24 amino acid residues from amino acid residues 62 to 85 of SEQ ID NO: 1, or from a sequence sharing at least 60%, 70%, 75%, 80%, 90%, 95%, 96%, 97%, 98%, 99% of identity over amino acid residues 62 to 85 of SEQ ID NO: 1.

In one embodiment, the antibody of the invention binds to a conformational epitope comprising or consisting of:
  the amino acid sequence as set forth in SEQ ID NO: 5 (LVALQGMSKRAVSTP) or an amino acid sequence sharing at least 60%, 70%, 75%, 80%, 90%, 95%, 96%, 97%, 98%, 99% of identity over SEQ ID NO: 5, and
  the amino acid sequence as set forth in SEQ ID NO: 4 (KDRSGDCSPETSLKQLRLKRDPGI) or an amino acid sequence sharing at least 60%, 70%, 75%, 80%, 90%, 95%, 96%, 97%, 98%, 99% of identity over SEQ ID NO: 4.

In some embodiments, the monoclonal antibody of the present invention binds to the extracellular domain of the CD160-TM isoform in the amino acid sequence as set forth in SEQ ID NO: 4 (KDRSGDCSPETSLKQLRLKRDPGI) and in the amino acid sequence as set forth in SEQ ID NO: 5 (LVALQGMSKRAVSTP).

The terms "monoclonal antibody", "monoclonal Ab", "monoclonal antibody composition", "mAb", or the like, as used herein refer to a preparation of antibody molecules of single molecular composition. A monoclonal antibody is obtained from a population of substantially homogeneous antibodies, i.e., the individual antibodies comprised in the population are identical except for possible naturally occurring mutations that may be present in minor amounts. A monoclonal antibody composition displays a single binding specificity and affinity for a particular epitope. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with the appropriate antigenic forms (i.e., CD160-TM polypeptides). The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes. However, the modifier "monoclonal" is not to be construed as requiring production of the antibody by any particular method. For example, a monoclonal antibody may also be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). A "monoclonal antibody" may also be isolated from phage antibody libraries using the techniques described in Clackson et al., Nature, 352:624-628 (1991) and Marks et al., J. Mol. Biol., 222: 581-597 (1991), for example.

In some embodiments, the monoclonal antibody of the invention is a chimeric antibody, in particular a chimeric mouse/human antibody. As used herein, the term "chimeric antibody" refers to an antibody which comprises a VH domain and a VL domain of a non-human antibody, and a CH domain and a CL domain of a human antibody. In one embodiment, a "chimeric antibody" is an antibody molecule in which (a) the constant region (i.e., the heavy and/or light chain), or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. Chimeric antibodies also include primatized and in particular humanized antibodies. Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992). (see U.S. Pat. No. 4,816,567; and Morrison et al., Proc. Natl. Acad. Sci. USA, 81:6851-6855 (1984)).

In some embodiments, the monoclonal antibody of the invention is a humanized antibody. In particular, in said humanized antibody, the variable domain comprises human acceptor frameworks regions, and optionally human constant domain where present, and non-human donor CDRs, such as mouse CDRs. According to the invention, the term "humanized antibody" refers to an antibody having variable region framework and constant regions from a human antibody but retains the CDRs of a previous non-human antibody. In one embodiment, a humanized antibody contains minimal sequence derived from non-human immunoglobulin. For the most part, humanized antibodies and antibody fragments thereof may be human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. Such antibodies are designed to maintain the binding specificity of the non-human antibody from which the binding regions are derived, but to avoid an immune reaction against the non-human antibody. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

In some embodiments, the monoclonal antibody is a human monoclonal antibody. As used herein the term "human monoclonal antibody", is intended to include antibodies having variable and constant regions derived from human immunoglobulin sequences. The human antibodies of the present invention may include amino acid residues not encoded by human immunoglobulin sequences (e.g., mutations introduced by random or site-specific mutagenesis in vitro or by somatic mutation in vivo). However, in one embodiment, the term "human monoclonal antibody", as used herein, is not intended to include antibodies in which CDR sequences derived from the germline of another mammalian species, such as a mouse, have been grafted onto human framework sequences.

In one embodiment, the antibody of the invention comprises a light chain comprising at least one or at least two of the following CDRs:
VL-CDR1: AGTSSDVGGY-$X_{11}$-$X_{12}$-VS, wherein $X_{11}$ is Y or S and $X_{12}$ is G or Y (SEQ ID NO: 6);
VL-CDR2: YDSYRPS (SEQ ID NO: 7); and
VL-CDR3: SS-$X_3$-TYYSTRV wherein $X_3$ is S or Y (SEQ ID NO: 8).

In one embodiment, the antibody of the invention comprises a light chain comprising the following CDRs:
VL-CDR1: AGTSSDVGGY-$X_{11}$-$X_{12}$-VS, wherein $X_{11}$ is Y or S and $X_{12}$ is G or Y (SEQ ID NO: 6);
VL-CDR2: YDSYRPS (SEQ ID NO: 7); and
VL-CDR3: SS-$X_3$-TYYSTRV wherein $X_3$ is S or Y (SEQ ID NO: 8).

In one embodiment, VL-CDR1 has a sequence selected from AGTSSDVGGYYGVS (SEQ ID NO: 20), AGTSSDVGGYYYVS (SEQ ID NO: 21), AGTSSDVGGYSGVS (SEQ ID NO: 22), and AGTSSDVGGYSYVS (SEQ ID NO: 23).

In one embodiment, VL-CDR3 is selected from SSSTYYSTRV (SEQ ID NO: 24) and SSYTYYSTRV (SEQ ID NO: 25).

In one embodiment, the antibody of the invention comprises a light chain comprising the three following CDRs:

VL-CDR1:
(SEQ ID NO: 20)
AGTSSDVGGYYGVS;

VL-CDR2:
(SEQ ID NO: 7)
YDSYRPS;
and

VL-CDR3:
(SEQ ID NO: 24)
SSSTYYSTRV.

In one embodiment, the antibody of the invention comprises a light chain comprising the three following CDRs:

VL-CDR1:
(SEQ ID NO: 20)
AGTSSDVGGYYGVS;

VL-CDR2:
(SEQ ID NO: 7)
YDSYRPS;
and

VL-CDR3:
(SEQ ID NO: 25)
SSYTYYSTRV.

In one embodiment, the antibody of the invention comprises a light chain comprising the three following CDRs:

VL-CDR1:
(SEQ ID NO: 21)
AGTSSDVGGYYYVS;

VL-CDR2:
(SEQ ID NO: 7)
YDSYRPS;
and

VL-CDR3:
(SEQ ID NO: 24)
SSSTYYSTRV.

In one embodiment, the antibody of the invention comprises a light chain comprising the three following CDRs:

VL-CDR1:
(SEQ ID NO: 21)
AGTSSDVGGYYYVS;

VL-CDR2:
(SEQ ID NO: 7)
YDSYRPS;
and

VL-CDR3:
(SEQ ID NO: 25)
SSYTYYSTRV.

In one embodiment, the antibody of the invention comprises a light chain comprising the three following CDRs:

VL-CDR1:
(SEQ ID NO: 22)
AGTSSDVGGYSGVS;

VL-CDR2:
(SEQ ID NO: 7)
YDSYRPS;
and

VL-CDR3:
(SEQ ID NO: 24)
SSSTYYSTRV.

In one embodiment, the antibody of the invention comprises a light chain comprising the three following CDRs:

```
VL-CDR1:
                                  (SEQ ID NO: 22)
AGTSSDVGGYSGVS;

VL-CDR2:
                                   (SEQ ID NO: 7)
YDSYRPS;
and

VL-CDR3:
                                  (SEQ ID NO: 25)
SSYTYYSTRV.
```

In one embodiment, the antibody of the invention comprises a light chain comprising the three following CDRs:

```
VL-CDR1:
                                  (SEQ ID NO: 23)
AGTSSDVGGYSYVS;

VL-CDR2:
                                   (SEQ ID NO: 7)
YDSYRPS;
and

VL-CDR3:
                                  (SEQ ID NO: 24)
SSSTYYSTRV.
```

In one embodiment, the antibody of the invention comprises a light chain comprising the three following CDRs:

```
VL-CDR1:
                                  (SEQ ID NO: 23)
AGTSSDVGGYSYVS;

VL-CDR2:
                                   (SEQ ID NO: 7)
YDSYRPS;
and

VL-CDR3:
                                  (SEQ ID NO: 25)
SSYTYYSTRV.
```

In one embodiment, the antibody of the invention comprises a heavy chain comprising at least one or at least two of the following CDRs:
VH-CDR1: NY-$X_3$-MN, wherein $X_3$ is S or Y (SEQ ID NO: 9)
VH-CDR2: $X_1$-IYGSSRYI-$X_{10}$-YADFVKG, wherein $X_1$ is Y or G and $X_{10}$ is N or S (SEQ ID NO: 10); and
VH-CDR3: GMDV (SEQ ID NO: 11).

In one embodiment, the antibody of the invention comprises a heavy chain comprising the following CDRs:
VH-CDR1: NY-$X_3$-MN, wherein $X_3$ is S or Y (SEQ ID NO: 9)
VH-CDR2: $X_1$-IYGSSRYI-$X_{10}$-YADFVKG, wherein $X_1$ is Y or G and $X_{10}$ is N or S (SEQ ID NO: 10); and
VH-CDR3: GMDV (SEQ ID NO: 11).

In one embodiment, VH-CDR1 has a sequence selected from NYSMN (SEQ ID NO: 26) and NYYMN (SEQ ID NO: 27).

In one embodiment, VH-CDR2 has a sequence selected from YIYGSSRYINYADFVKG (SEQ ID NO: 28), YIYGSSRYISYADFVKG (SEQ ID NO: 29), GIYGSSRYINYADFVKG (SEQ ID NO: 30) and GIYGSSRYISYADFVKG (SEQ ID NO: 31).

In one embodiment, the antibody of the invention comprises a heavy chain comprising the three following CDRs:

```
VH-CDR1:
                                  (SEQ ID NO: 26)
NYSMN;

VH-CDR2:
                                  (SEQ ID NO: 28)
YIYGSSRYINYADFVKG;
and

VH-CDR3:
                                  (SEQ ID NO: 11)
GMDV.
```

In one embodiment, the antibody of the invention comprises a heavy chain comprising the three following CDRs:

```
VH-CDR1:
                                  (SEQ ID NO: 26)
NYSMN;

VH-CDR2:
                                  (SEQ ID NO: 29)
YIYGSSRYISYADFVKG;
and

VH-CDR3:
                                  (SEQ ID NO: 11)
GMDV.
```

In one embodiment, the antibody of the invention comprises a heavy chain comprising the three following CDRs:

```
VH-CDR1:
                                  (SEQ ID NO: 26)
NYSMN;

VH-CDR2:
                                  (SEQ ID NO: 30)
GIYGSSRYINYADFVKG;
and

VH-CDR3:
                                  (SEQ ID NO: 11)
GMDV.
```

In one embodiment, the antibody of the invention comprises a heavy chain comprising the three following CDRs:

```
VH-CDR1:
                                  (SEQ ID NO: 26)
NYSMN;

VH-CDR2:
                                  (SEQ ID NO: 31)
GIYGSSRYISYADFVKG;
and

VH-CDR3:
                                  (SEQ ID NO: 11)
GMDV.
```

In one embodiment, the antibody of the invention comprises a heavy chain comprising the three following CDRs:

```
VH-CDR1:
                                  (SEQ ID NO: 27)
NYYMN;

VH-CDR2:
                                  (SEQ ID NO: 28)
YIYGSSRYINYADFVKG;
and
```

-continued

VH-CDR3:
(SEQ ID NO: 11)
GMDV.

In one embodiment, the antibody of the invention comprises a heavy chain comprising the three following CDRs:

VH-CDR1:
(SEQ ID NO: 27)
NYYMN;

VH-CDR2:
(SEQ ID NO: 29)
YIYGSSRYISYADFVKG;
and

VH-CDR3:
(SEQ ID NO: 11)
GMDV.

In one embodiment, the antibody of the invention comprises a heavy chain comprising the three following CDRs:

VH-CDR1:
(SEQ ID NO: 27)
NYYMN;

VH-CDR2:
(SEQ ID NO: 30)
GIYGSSRYINYADFVKG;
and

VH-CDR3:
(SEQ ID NO: 11)
GMDV.

In one embodiment, the antibody of the invention comprises a heavy chain comprising the three following CDRs:

VH-CDR1:
(SEQ ID NO: 27)
NYYMN;

VH-CDR2:
(SEQ ID NO: 31)
GIYGSSRYISYADFVKG;
and

VH-CDR3:
(SEQ ID NO: 11)
GMDV.

In some embodiments, the monoclonal antibody of the present invention comprises a light chain comprising i) the VL-CDR1 as set forth in SEQ ID NO: 6 wherein $X_{11}$ is Y or S and $X_{12}$ is G or Y, ii) the VL-CDR2 as set forth in SEQ ID NO: 7 and iii) the VL-CDR3 as set forth in SEQ ID NO: 8 wherein $X_3$ is S or Y, and a heavy chain comprising i) the VH-CDR1 as set forth in SEQ ID NO: 9 wherein $X_3$ is S or Y, ii) the VH-CDR2 as set forth in SEQ ID NO: 10 wherein $X_1$ is Y or G and $X_{10}$ is N or S and iii) the VH-CDR3 as set forth in SEQ ID NO: 11.

According to the invention, any of the CDRs 1, 2 and 3 of the heavy and light chains may be characterized as having an amino acid sequence that shares at least 60%, 70%, 75%, 80%, 90%, 95%, 96%, 97%, 98%, 99% of identity with the particular CDR or sets of CDRs listed in the corresponding SEQ ID NO.

In some embodiments, the monoclonal antibody of the present invention comprises a light chain comprising i) the VL-CDR1 of A12, ii) the VL-CDR2 of A12 and iii) the VL-CDR3 of A12, and a heavy chain comprising i) the VH-CDR1 of A12, ii) the VH-CDR2 of A12 and iii) the VH-CDR3 of A12.

According to the present invention, the VH region of the A12 antibody consists of the sequence of SEQ ID NO: 12. Accordingly, the VH-CDR1 of A12 is defined by the sequence ranging from the amino acid residue at position 31 to the amino acid residue at position 35 in SEQ ID NO: 12. Accordingly, the VH-CDR2 of A12 is defined by the sequence ranging from the amino acid residue at position 50 to the amino acid residue at position 66 in SEQ ID NO: 12. Accordingly, the VH-CDR3 of A12 is defined by the sequence ranging from the amino acid residue at position 103 to the amino acid residue at position 106 in SEQ ID NO: 12.

SEQ ID NO: 12: VH region of A12 antibody FR1-CDR1-
FR2-CDR2-FR3-CDR3-FR4
EVQLVESGGSLVKPGGSLRLSCAASGFTF<u>SNYSMN</u>WVRQAPGKGLEWIS
<u>YIYGSSRYISYADFVKG</u>RFTISRDNATNSLYLQMNSLRAEDTAVYYCVR
SYYG<u>GMDV</u>WGRGTLVTVSS According to the present invention, the VL region of the A12 antibody consists of the sequence of SEQ ID NO: 13. Accordingly, the VL-CDR1 of A12 is defined by the sequence ranging from the amino acid residue at position 23 to the amino acid residue at position 36 in SEQ ID NO: 13. Accordingly, the VL-CDR2 of A12 is defined by the sequence ranging from the amino acid residue at position 52 to the amino acid residue at position 58 in SEQ ID NO: 13. Accordingly, the VL-CDR3 of A12 is defined by the sequence ranging from the amino acid residue at position 91 to the amino acid residue at position 100 in SEQ ID NO: 13.

SEQ ID NO: 13: VL region of A12 antibody FR1-CDR1-
FR2-CDR2-FR3-CDR3-FR4
QSVLTQPASVSGSPGQSITISC<u>AGTSSDVGGYYGVS</u>WYQQHPGKAPKLMI
<u>YYDSYRPS</u>GVSNRFSGSKSGNTASLTISGLQAEDEADYYC<u>SSSTYYSTRV</u>
FGGGTKLEK In one embodiment, the light chain of the A12 antibody comprises the following CDR: i) VL-CDR1: SEQ ID NO: 20, ii) VL-CDR2: SEQ ID NO: 7 and iii) VL-CDR3: SEQ ID NO: 24, and the heavy chain of the A12 antibody comprises the following CDR i) VH-CDR1: SEQ ID NO: 26, ii) VH-CDR2: SEQ ID NO: 29 and iii) VH-CDR3: SEQ ID NO: 11.

In some embodiments, the monoclonal antibody of the present invention comprises a light chain comprising i) the VL-CDR1 of B6, ii) the VL-CDR2 of B6 and iii) the VL-CDR3 of B6, and a heavy chain comprising i) the VH-CDR1 of B6, ii) the VH-CDR2 of B6 and iii) the VH-CDR3 of B6.

According to the present invention, the VH region of the B6 antibody consists of the sequence of SEQ ID NO: 14. Accordingly, the VH-CDR1 of B6 is defined by the sequence ranging from the amino acid residue at position 31 to the amino acid residue at position 35 in SEQ ID NO: 14. Accordingly, the VH-CDR2 of B6 is defined by the sequence ranging from the amino acid residue at position 50 to the amino acid residue at position 66 in SEQ ID NO: 14. Accordingly, the VH-CDR3 of B6 is defined by the sequence ranging from the amino acid residue at position 103 to the amino acid residue at position 106 in SEQ ID NO: 14.

SEQ ID NO: 14: VH region of B6 antibody FR1-CDR1-
FR2-CDR2-FR3-CDR3-FR4
EVQLVESGGSLVKPGGSLRLSCAASGFTFS<u>NYYMN</u>WVRQAPGKGLEWIS
<u>GIYGSSRYINYADFVKG</u>RFTISRDNATNSLYLQMNSLRAEDTAVYYCVR
SYYG<u>GMDV</u>WGRGTLVTSS According to the present invention, the VL region of the B6 antibody consists of the sequence of SEQ ID NO: 15. Accordingly, the VL-CDR1 of B6 is defined by the sequence ranging from the amino acid residue at position 23 to the amino acid residue at position 36 in SEQ ID NO: 15. Accordingly, the VL-CDR2 of B6 is defined by the sequence ranging from the amino acid residue at position 52 to the amino acid residue at position 58 in SEQ ID NO: 15. Accordingly, the VL-CDR3 of B6 is defined by the sequence ranging from the amino acid residue at position 91 to the amino acid residue at position 100 in SEQ ID NO: 15.

SEQ ID NO: 15: VL region of B6 antibody FR1-CDR1-
FR2-CDR2-FR3-CDR3-FR4
QSVLTQPASVSGSPGQSITISC<u>AGTSSDVGGYSYVS</u>WYQQHPGKAPKLMI
YY<u>DSYRPS</u>GVSNRFSGSKSGNTASLTISGLQAEDEADYYC<u>SSYTYYSTRV</u>
FGGGTKLEK In one embodiment, the light chain of the B6 antibody comprises the following CDR: i) VL-CDR1: SEQ ID NO: 23, ii) VL-CDR2: SEQ ID NO: 7 and iii) VL-CDR3: SEQ ID NO: 25, and the heavy chain of the B6 antibody comprises the following CDR i) VH-CDR1: SEQ ID NO: 27, ii) VH-CDR2: SEQ ID NO: 30 and iii) VH-CDR3: SEQ ID NO: 11.

In some embodiments, the human monoclonal antibody of the present invention is an antibody comprising a heavy chain having at least 70% of identity with SEQ ID NO: 12 or SEQ ID NO: 14.

In some embodiments, the human monoclonal antibody of the present invention is an antibody comprising a light chain having at least 70% of identity with SEQ ID NO: 13 or SEQ ID NO: 15.

In some embodiments, the human monoclonal antibody of the present invention is an antibody comprising a heavy chain having at least 70% of identity with SEQ ID NO: 12 or SEQ ID NO: 14 and a light chain having at least 70% of identity with SEQ ID NO: 13 or SEQ ID NO: 15.

According to the invention, a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; 99 or 100% of identity with the second amino acid sequence. Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

In some embodiments, the human monoclonal antibody of the present invention is an antibody comprising a heavy chain which is identical to SEQ ID NO: 12 or SEQ ID NO: 14.

In some embodiments, the human monoclonal antibody of the present invention is an antibody comprising a light chain identical to SEQ ID NO: 13 or SEQ ID NO: 15.

In some embodiments, the human monoclonal antibody of the present invention is an antibody comprising a heavy chain identical to SEQ ID NO: 12 or SEQ ID NO: 14 and a light chain identical to SEQ ID NO: 13 or SEQ ID NO: 15.

In one embodiment, the human monoclonal antibody of the present invention is an antibody comprising a heavy chain identical to SEQ ID NO: 12 and a light chain identical to SEQ ID NO: 13. In one embodiment, the human monoclonal antibody of the present invention is an antibody comprising a heavy chain identical to SEQ ID NO: 12 and a light chain identical to SEQ ID NO: 15. In one embodiment, the human monoclonal antibody of the present invention is an antibody comprising a heavy chain identical to SEQ ID NO: 14 and a light chain identical to SEQ ID NO: 13. In one embodiment, the human monoclonal antibody of the present invention is an antibody comprising a heavy chain identical to SEQ ID NO: 14 and a light chain identical to SEQ ID NO: 15.

In one embodiment, the heavy chain and/or the light chain of the antibody of the invention comprises conservative sequence modifications as compared to the SEQ ID NO defined hereinabove, for example 1 to 10 conservative sequence modifications. The term "conservative sequence modifications" refers to amino acid modifications that do not significantly affect or alter the biologic function of the protein containing the amino acid sequence. Such conservative modifications include amino acid substitutions, additions and deletions. Modifications can be introduced into a protein by standard techniques known in the art, such as site-directed mutagenesis and PCR-mediated mutagenesis. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine. Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Other families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within an antibody of the invention can be replaced with other amino acid residues from the same side chain family and the altered antibody can be tested for binding to CD160-TM.

In some embodiments, the monoclonal antibody of the present invention is selected from the group of Fab, F(ab')$_2$, Fab' and scFv. As used herein, the term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond. The term "F(ab')$_2$" refers to an antibody fragment having a molecular weight of about 100,000 and antigen binding activity, which is slightly larger than the Fab bound via a disulfide bond of the hinge region, among fragments obtained by treating IgG with a protease, pepsin. The term "Fab'" refers to an antibody fragment having a molecular weight of about 50,000 and antigen binding activity, which is obtained by cutting a disulfide bond of the hinge region of the F(ab')$_2$. Fab'-SH is the designation herein for Fab' in which the cysteine residue(s) of the constant domains bear a free thiol group. A single chain Fv ("scFv") polypeptide is a covalently linked VH::VL heterodimer which is usually expressed from a gene fusion including VH and VL encoding genes linked by a peptide-encoding linker. The scFv fragment of the invention includes CDRs that are held in appropriate conformation, preferably by using gene recombination techniques.

In some embodiments, the monoclonal antibody of the present invention cross-competes for binding to the CD160-TM isoform with the monoclonal antibody which comprises a light chain comprising i) the VL-CDR1 as set forth in SEQ ID NO: 6 wherein $X_{11}$ is Y or S and $X_{12}$ is G or Y, ii) the VL-CDR2 as set forth in SEQ ID NO: 7 and iii) the VL-CDR3 as set forth in SEQ ID NO: 8 wherein $X_3$ is S or Y, and a heavy chain comprising i) the VH-CDR1 as set forth in SEQ ID NO: 9 wherein $X_3$ is S or Y, ii) the VH-CDR2 as set forth in SEQ ID NO: 10 wherein $X_1$ is Y or G and $X_{10}$ is N or S (SEQ ID NO: 10) and iii) the VH-CDR3 as set forth in SEQ ID NO: 11.

In some embodiments, the monoclonal antibody of the present invention cross-competes for binding to the CD160-TM isoform with the monoclonal antibody which comprises the CDRs of A12 as defined above.

In some embodiments, the monoclonal antibody of the present invention cross-competes for binding to the CD160-TM isoform with the monoclonal antibody which comprises CDRs of B6 as defined above.

The term "cross-competes" refers to monoclonal antibodies which share the ability to bind to a specific region of an antigen. In the present disclosure the monoclonal antibody that "cross-competes" has the ability to interfere with the binding of another monoclonal antibody for the antigen in a standard competitive binding assay. Such a monoclonal antibody may, according to non-limiting theory, bind to the same or a related or nearby (e.g., a structurally similar or spatially proximal) epitope as the antibody with which it competes. Cross-competition is present if antibody A reduces binding of antibody B at least by 60%, specifically at least by 70% and more specifically at least by 80% and vice versa in comparison to the positive control which lacks one of said antibodies. As the skilled artisan appreciates competition may be assessed in different assay set-ups. One suitable assay involves the use of the Biacore technology (e.g., by using the BIAcore 3000 instrument (Biacore, Uppsala, Sweden)), which can measure the extent of interactions using surface plasmon resonance technology. Another assay for measuring cross-competition uses an ELISA-based approach. Furthermore a high throughput process for "binning" antibodies based upon their cross-competition is described in International Patent Application No. WO2003/48731.

According to the present invention, the cross-competing antibody as above described retain the activity of the monoclonal antibody which comprises a light chain comprising i) the VL-CDR1 as set forth in SEQ ID NO: 6 wherein $X_{11}$ is Y or S and $X_{12}$ is G or Y, ii) the VL-CDR2 as set forth in SEQ ID NO: 7 and iii) the VL-CDR3 as set forth in SEQ ID NO: 8 wherein $X_3$ is S or Y, and a heavy chain comprising i) the VH-CDR1 as set forth in SEQ ID NO: 9 wherein $X_3$ is S or Y, ii) the VH-CDR2 as set forth in SEQ ID NO: 10 wherein $X_1$ is Y or G and $X_{10}$ is N or S and iii) the VH-CDR3 as set forth in SEQ ID NO: 11. In particular, the cross-competing antibody retains the activity of the A12 or B6 antibody. Any assay well known in the art would be suitable for identifying whether the cross-competing antibody retains the desired activity. For instance the assay described in EXAMPLE 4 that consist in determining the ability of increasing degranulation activity of the antibody would be suitable for determining whether the antibody retains the ability of increasing the NK cells activities, in particular NK cell killing activities.

As shown in EXAMPLE 1, the monoclonal antibody of the present invention does not cross-compete with the CL1-R2 antibody for binding to the CD160 GPI-anchored isoform. Conversely, the CL1-R2 antibody does not cross-compete with the monoclonal antibody of the present invention for binding to the CD160-TM isoform. CL1-R2 antibody is obtainable by the hybridoma deposited at the Collection Nationale de Cultures de Microorganismes C.N.C.M. Institut Pasteur in accordance with the terms of the Budapest Treaty on Apr. 28, 2004 (C.N.C.M. Institut Pasteur 25, rue du Docteur Roux F-75724 Paris Cedex 15 France). The deposited hybridoma has CNCM deposit number 1-3204.

Furthermore, as shown in EXAMPLE 1, the monoclonal antibody of the present invention does not cross-compete with the BY55 antibody for binding to the CD160 GPI-anchored isoform. Conversely, the BY55 antibody does not cross-compete with the monoclonal antibody of the present invention for binding to the CD160-TM isoform. BY55 may be obtained, for example, from Abcam (reference number ab81388) and from ThermoFisher Scientific (reference number 12-1609-42).

In one embodiment, the invention also provides an antibody that binds essentially the same epitope as A12 or B6 antibodies as described hereinabove. In the present invention, an antibody that binds essentially the same epitope as A12 or B6 antibodies will be referred as an A12-like or B6-like antibody, respectively.

The antibodies of the present invention are produced by any technique known in the art, such as, without limitation, any chemical, biological, genetic or enzymatic technique, either alone or in combination. Typically, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the present invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the invention relates to a nucleic acid molecule encoding an antibody according to the invention. More particularly the nucleic acid molecule encodes a heavy chain or a light chain of an antibody of the present invention. More particularly the nucleic acid molecule comprises a nucleic acid sequence having 70% of identity with SEQ ID NO: 16, SEQ ID NO: 17, SEQ ID NO: 18 or SEQ ID NO: 19.

```
Heavy chain: DNA sequence of A12
                                        SEQ ID NO: 16
AGGTGCAGCTGGTGGAGTCTGGGGGAAGCCTGGTCAAGCCTGGGGGGTC

CCTGAGACTCTCCTGTGCAGCTCTGGATTCACCTTCAGTAACTATAGTA

TGAACTGGGTCCGCCAGGCTCCAGGGAAGGGCTGGAGTGGATCTCATAT

ATTTATGGTAGTAGTAGATATATAAGTTACGCAGACTTCGTGAAGGGCG

ATTCACCATCTCCAGAGACAACGCCACGAACTCACTGTACCTGCAAATG

AACAGCCTAGAGCCGAGGACACGGCTGTTTATTACTGTGTGAGATCCTA

TTATGGCGGTATGGACGTCTGGGGCAGGGCACCCTGGTCACCGTCTCCT

CA

Light chain: DNA sequence of A12
                                        SEQ ID NO: 17
CAGTCTGTGCTGACTCAGCCTGCCTCCGTGTCTGGGTCTCCTGGACAGT

CGATCACCATCTCCTGCGCTGAACCAGCAGTGACGTTGGTGGTTATTAT

GGCGTCTCCTGGTACCAACAACACCCAGGAAAGCCCCCAAACTCATGAT
```

```
-continued
TTATTATGACAGTTATCGGCCCTCAGGGGTTTCTAATCGCTTCTCTGGC

CCAAGTCTGGCAACACGGCCTCCCTGACAATCTCTGGGCTCCAGGCTGA

GGACGAGGCGATTATTACTGCAGCTCAAGTACATATTATAGCACTCGAG

TTTTCGGCGGAGGGACCAAGCTGGAGATAAA

Heavy chain: DNA sequence of B6
                                        SEQ ID NO: 18
GAGGTGCAGCTGGTGGAGTCTGGGGGAAGCCTGGTCAAGCCTGGGGGGT

CCCTGAGACTCTCCTGTGCAGCCTCTGGATTCACCTTCAGTAACTATTA

TATGAACTGGGTCCGCCAGGCTCCAGGGAAGGGGCTGGAGTGGATCTCA

GGCATTTATGGTAGTAGTAGATATATAAACTACGCAGACTTCGTGAAGG

GCCGATTCACCATCTCCAGAGACAACGCCACGAACTCACTGTACCTGCA

AATGAACAGCCTGAGAGCCGAGGACACGGCTGTTTATTACTGTGTGAGA

TCCAGTGGCTATGGCGGTATGGACGTCTGGGGCAGAGGCACCCTGGTCA

CCGTCTCCTCA

Light chain: DNA sequence of B6
                                        SEQ ID NO: 19
CAGTCTGTGCTGACTCAGCCTGCCTCCGTGTCTGGGTCTCCTGGACAGT

CGATCACCATCTCCTGCGCTGGAACCAGCAGTGACGTTGGTGGTTATAG

TTATGTCTCCTGGTACCAACAACACCCAGGCAAAGCCCCCAAACTCATG

ATTTATTATGACAGTTATCGGCCCTCAGGGGTTTCTAATCGCTTCTCTG

GCTCCAAGTCTGGCAACACGGCCTCCCTGACAATCTCTGGGCTCCAGGC

TGAGGACGAGGCTGATTATTACTGCAGCTCATATACATATTATAGCACT

CGAGTTTTCGGCGGAGGGACCAAGCTGGAGATCAAA
```

The term "encoding" refers to the inherent property of specific sequences of nucleotides in a polynucleotide, such as, for example, a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. The phrase "nucleotide sequence that encodes a protein or a RNA" may also include introns to the extent that the nucleotide sequence encoding the protein may in some version contain an intron(s).

Typically, said nucleic acid is a DNA or RNA molecule, which may be included in any suitable vector, such as a plasmid, cosmid, episome, artificial chromosome, phage or a viral vector. As used herein, the terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence. So, a further object of the invention relates to a vector comprising a nucleic acid of the invention. Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40, LTR promoter and enhancer of Moloney mouse leukemia virus, promoter and enhancer of immunoglobulin H chain and the like. Any expression vector for animal cell can be used, so long as a gene encoding the human antibody C region can be inserted and expressed. Examples of suitable vectors include pAGE107, pAGE103, pHSG274, pKCR, pSG1 beta d2-4 and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

The term "promoter/regulatory sequence" refers to a nucleic acid sequence (such as, for example, a DNA sequence) recognized by the synthetic machinery of the cell, or introduced synthetic machinery, required to initiate the specific transcription of a polynucleotide sequence, thereby allowing the expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

A further object of the present invention relates to a host cell which has been transfected, infected or transformed by a nucleic acid and/or a vector according to the invention. As used herein, the term "transformation" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce an antibody of the present invention in a suitable expression system. The term "expression system" means a host cell and compatible vector under suitable conditions, e.g., for the expression of a protein coded for by foreign DNA carried by the vector and introduced to the host cell. Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli*, *Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like. The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present invention.

Examples of vectors include all those known in the art, including, without limitation, cosmids, plasmids (e.g., naked or contained in liposomes) and viruses (e.g., lentiviruses, retroviruses, adenoviruses, and adeno-associated viruses) that incorporate the recombinant polynucleotide.

Antibodies of the present invention are suitably separated from the culture medium by conventional immunoglobulin purification procedures such as, for example, protein A-Sepharose, hydroxylapatite chromatography, gel electrophoresis, dialysis, or affinity chromatography.

The present invention further relates to a composition comprising, consisting of or consisting essentially of an antibody of the present invention, preferably a B6-like or A12-like antibody.

As used herein, "consisting essentially of", with reference to a composition, means that the at least one antibody of the invention as described hereinabove is the only one therapeutic agent or agent with a biologic activity within said composition.

In one embodiment, the composition of the invention is a pharmaceutical composition and further comprises a pharmaceutically acceptable carrier.

The present invention further relates to a medicament comprising, consisting of or consisting essentially of an antibody of the present invention, preferably a B6-like or A12-like antibody.

Engineered antibodies of the present invention include those in which modifications have been made to framework residues within VH and/or VL, e.g., to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In some embodiments, the antibody (preferably the monoclonal antibody) of the present invention comprises a Fc region that mediates antibody-dependent cell-mediated cytotoxicity. As used herein the term "antibody-dependent cell-mediated cytotoxicity" or 'ADCC" refer to a cell-mediated reaction in which non-specific cytotoxic cells (e.g., Natural Killer (NK) cells, neutrophils, and macrophages) recognize bound antibody on a target cell and subsequently cause lysis of the target cell. While not wishing to be limited to any particular mechanism of action, these cytotoxic cells that mediate ADCC generally express Fc receptors (FcRs).

As used herein "Fc region" includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al. supra. Fc may refer to this region in isolation, or this region in the context of an antibody, antibody fragment, or Fc fusion protein. An Fc variant protein may be an antibody, Fc fusion, or any protein or protein domain that comprises an Fc region. Particularly preferred are proteins comprising variant Fc regions, which are non-naturally occurring variants of an Fc region. The amino acid sequence of a non-naturally occurring Fc region (also referred to herein as a "variant Fc region") comprises a substitution, insertion and/or deletion of at least one amino acid residue compared to the wild type amino acid sequence. Any new amino acid residue appearing in the sequence of a variant Fc region as a result of an insertion or substitution may be referred to as a non-naturally occurring amino acid residue. Note: Polymorphisms have been observed at a number of Fc positions, including but not limited to Kabat 270, 272, 312, 315, 356, and 358, and thus slight differences between the presented sequence and sequences in the prior art may exist.

The terms "Fc receptor" or "FcR" are used to describe a receptor that binds to the Fc region of an antibody. The primary cells for mediating ADCC, NK cells, express FcγRIII, whereas monocytes express FcγRI, FcγRII, FcγRIII and/or FcγRIV. FcR expression on hematopoietic cells is summarized in Ravetch and Kinet, Annu. Rev. Immunol., 9:457-92 (1991). To assess ADCC activity of a molecule, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., Proc. Natl. Acad. Sci. (USA), 95:652-656 (1998). As used herein, the term "effector cells" are leukocytes which express one or more FcRs and perform effector functions. The cells express at least FcγRI, FCγRII, FcγRIII and/or FcγRIV and carry out ADCC effector function. Examples of human leukocytes which mediate ADCC include peripheral blood mononuclear cells (PBMC), natural killer (NK) cells, monocytes, cytotoxic T cells and neutrophils.

In some embodiments, the antibody (preferably the monoclonal antibody) of the present invention is a full-length antibody. In some embodiments, the full-length antibody is an IgG1 antibody. In some embodiments, the full-length antibody is an IgG3 antibody.

In some embodiments, the antibody (preferably the monoclonal antibody) of the present invention comprises a variant Fc region that has an increased affinity for FcγRIA, FcγRIIA, FcγRIIB, FcγRIIIA, FcγRIIIB, and FcγRIV. In some embodiments, the antibody (preferably the monoclonal antibody) of the present invention comprises a variant Fc region comprising at least one amino acid substitution, insertion or deletion wherein said at least one amino acid residue substitution, insertion or deletion results in an increased affinity for FcγRIA, FcγRIIA, FcγRIIB, FcγRIIIA, FcγRIIIB, and FcγRIV. In some embodiments, the antibody (preferably the monoclonal antibody) of the present invention comprises a variant Fc region comprising at least one amino acid substitution, insertion or deletion wherein said at least one amino acid residue is selected from the group consisting of: residue 239, 330, and 332, wherein amino acid residues are numbered following the EU index. In some embodiments, the antibody (preferably the monoclonal antibody) of the present invention comprises a variant Fc region comprising at least one amino acid substitution wherein said at least one amino acid substitution is selected from the group consisting of: S239D, A330L, A330Y, and I332E, wherein amino acid residues are numbered following the EU index.

In some embodiments, the glycosylation of the antibody of the present invention is modified. For example, an aglycoslated antibody can be made (i.e., the antibody lacks glycosylation). Glycosylation can be altered to, for example, increase the affinity of the antibody for the antigen or alter the ADCC activity of the antibody. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al (incorporated herein by reference). Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered fucosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present invention to thereby produce an antibody with altered glycosylation. For example, EP1176195 by Hang et al. (incorporated herein by reference) describes a cell line with a functionally disrupted FUT8 gene, which encodes a fucosyl transferase, such that antibodies expressed in such a cell line exhibit hypofucosylation or are devoid of fucosyl residues. Therefore, in some embodiments, the human antibody (preferably the monoclonal antibody) of the present invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta (incorporated herein by reference) describes a variant CHO cell line, Lec13 cells, with reduced ability to attach fucose to Asn(297)-linked carbohydrates, also resulting in hypofucosylation of antibodies expressed in that host cell (see also Shields, R. L. et al, 2002 J. Biol. Chem. 277:26733-26740). PCT Publication WO 99/54342 by Umana et al. (incorporated herein by reference) describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al, 1999 Nat. Biotech. 17: 176-180). Eureka Therapeutics further describes genetically engineered CHO mammalian cells capable of producing antibodies with altered mammalian glycosylation pattern devoid of fucosyl residues (www.eurekainc.com/a&boutus/companyoverview.html). Alternatively, the human antibody (preferably the monoclonal antibody) of the present invention can be produced in yeasts or filamentous fungi engineered for mammalian-like glycosylation pattern and capable of producing antibodies lacking fucose as glycosylation pattern (see for example EP1297172B1).

In some embodiments, the antibody (preferably the monoclonal antibody) of the present invention comprises a Fc region that mediates complement dependant cytotoxicity. "Complement dependent cytotoxicity" or "CDC" refers to the ability of a molecule to initiate complement activation and lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santaro et al., J. Immunol. Methods, 202:163 (1996), may be performed.

In some embodiments, the antibody (preferably the monoclonal antibody) of the present invention comprises a Fc region that mediates antibody-dependent phagocytosis. As used herein, the term "antibody-dependent phagocytosis" or "opsonisation" refers to the cell-mediated reaction wherein nonspecific cytotoxic cells that express FcγRs recognize bound antibody on a target cell and subsequently cause phagocytosis of the target cell.

In one embodiment, the antibody (preferably the monoclonal antibody) of the present invention comprises a Fc region inducing ADCC or CDC or antibody-dependent phagocytosis. Consequently, administration of such antibody to a subject may lead to the depletion of cells expressing CD160-TM (e.g., leads to a 10%, 20%, 50%, 60% or greater elimination or decrease in number of CD160-TM$^+$ NK cells), such as, for example CD160-TM expressing tumor cells.

A further object of the present invention thus relates to a method of depleting a population of cells which express the CD160-TM isoform in a subject in need thereof comprising delivering to the subject a therapeutically effective amount of the antibody (preferably the monoclonal antibody) of the present invention. In one embodiment, the antibody (preferably the monoclonal antibody) of the present invention comprises a Fc region inducing ADCC or CDC or antibody-dependent phagocytosis.

A further object of the present invention relates to a method of depleting a population of malignant NK cells which express the CD160-TM isoform in a subject in need thereof comprising delivering to the subject a therapeutically effective amount of the antibody (preferably the monoclonal antibody) of the present invention. In one embodiment, the antibody (preferably the monoclonal antibody) of the present invention comprises a Fc region inducing ADCC or CDC or antibody-dependent phagocytosis.

A further object of the present invention relates to a method of depleting a population of cells which express the epitope recognized by the A12 or B6 antibody in in a subject in need thereof comprising delivering to the subject a therapeutically effective amount of the antibody (preferably the monoclonal antibody) of the present invention. In one embodiment, the antibody (preferably the monoclonal antibody) of the present invention comprises a Fc region inducing ADCC or CDC or antibody-dependent phagocytosis.

As used herein, the term "deplete" with respect to a population of cells, refers to a measurable decrease in the number of said cells in the subject. The reduction can be at least about 10%, e.g., at least about 20%, 30%, 40%, 50%, 60%, 70%, 80%, 90%, 95%, 96%, 97%, 98%, 99%, or more. In some embodiments, the term refers to a decrease in the number of the cells in a subject or in a sample to an amount below detectable limits.

In one embodiment, the antibody (preferably the monoclonal antibody) of the present invention mediates antibody dependent cellular cytotoxicity, complement dependent cytotoxicity and antibody-dependent phagocytosis.

A further object of the present invention relates to a method of treating a cancer wherein cancer cells express CD160-TM. In particular, examples of cancers wherein cancer cells express CD160-TM include, but are not limited to, a NK leukemia or a NK lymphoma, such as for example, extranodal and non-extranodal NK/T lymphomas; NK cell derived malignancies; and acute NK leukemia.

The present invention thus further relates to an antibody, a composition, a pharmaceutical composition or a medicament of the present invention for use in treating a cancer wherein cancer cells express CD160-TM.

In some embodiments, the antibody (preferably the monoclonal antibody) of the present invention does not comprise a Fc region that mediates antibody-dependent cell-mediated cytotoxicity and thus does not comprise an Fc portion that induces antibody dependent cellular cytotoxicity (ADCC). In one embodiment, the antibody (preferably the monoclonal antibody) of the present invention does not comprise an Fc region that induces CDC or antibody-dependent phagocytosis. In some embodiments the antibody (preferably the monoclonal antibody) of the present invention does not lead, directly or indirectly, to the depletion of NK cells expressing CD160-TM polypeptides (e.g., do not lead to a 10%, 20%, 50%, 60% or greater elimination or decrease in number of CD160-TM$^+$ NK cells). In some embodiments, the antibody (preferably the monoclonal antibody) of the present invention does not comprise an Fc domain capable of substantially binding to a FcγRIIIA (CD16) polypeptide. In some embodiments, the antibody (preferably the monoclonal antibody) of the present invention lacks an Fc domain (e.g., lacks a CH2 and/or CH3 domain) or comprises an Fc domain of IgG2 or IgG4 isotype. In some embodiments, the antibody (preferably the monoclonal antibody) of the present invention comprises an Fc domain (e.g. of IgG1) with an altered glycosylation profile, resulting in the absence of ADCC activity of the antibody. In some embodiments, the antibody (preferably the monoclonal antibody) of the present invention consists of or comprises a Fab, Fab', Fab'-SH, F(ab')$_2$, Fv, a diabody, single-chain antibody fragment, or a multispecific antibody comprising multiple different antibody fragments. In some embodiments, the antibody (preferably the monoclonal antibody) of the present invention is not linked to a toxic moiety. In some embodiments, one or more amino acids selected from amino acid residues can be replaced with a different amino acid residue such that the antibody has altered C2q binding and/or reduced or abolished complement dependent cytotoxicity (CDC). This approach is described in further detail in U.S. Pat. No. 6,194,551 by Idusogie et al.

A further object of the present invention relates to a method of enhancing NK cell activities or NK cell effector functions, in particular NK cell killing activities in a subject in need thereof comprising administering to the subject a therapeutically effective amount of an antibody of the present invention, provided that the antibody does not mediate antibody dependent cellular cytotoxicity, complement dependent cytotoxicity or antibody-dependent phagocytosis.

As used herein, "NK cells" refers to a sub-population of lymphocytes that is involved in innate or non-conventional immunity. NK cells can be identified by virtue of certain characteristics and biological properties, such as the expression of specific surface antigens including CD56 and/or CD16 for human NK cells, the absence of the alpha/beta or gamma/delta TCR complex on the cell surface, the ability to bind to and kill cells that fail to express "self" MHC/HLA antigens by the activation of specific cytolytic machinery, the ability to kill tumor cells or other diseased cells that express a ligand for NK activating receptors, and the ability to release protein molecules called cytokines that stimulate or inhibit the immune response ("NK cell activities"). Any subpopulation of NK cells will also be encompassed by the term NK cells. Within the context of this invention "active" NK cells designate biologically active NK cells, including NK cells having the capacity of lysing target cells or enhancing the immune function of other cells. For instance, an "active" NK cell can be able to kill cells that express a ligand for an activating NK receptor and/or fail to express MHC/HLA antigens recognized by a MR on the NK cell.

The ability of the antibody (preferably the monoclonal antibody) of the present invention to enhance NK cell activities, in particular NK cell killing activities, may be determined by any assay well known in the art. Typically said assay is an in vitro assay wherein NK cells are brought into contact with target cells (e.g., target cells that are recognized and/or lysed by NK cells). For example, the antibody can be selected for the ability to increase specific lysis by NK cells by more than about 20%, preferably with at least about 30%, at least about 40%, at least about 50%, or more of the specific lysis obtained at the same effector: target cell ratio with NK cells or NK cell lines that are contacted by the antibody (preferably the monoclonal antibody) of the present invention. Examples of protocols for classical cytotoxicity assays are described, for example, in Pessino et al, J. Exp. Med, 1998, 188 (5): 953-960; Sivori et al, Eur J Immunol, 1999. 29:1656-1666; Brando et al, (2005) J. Leukoc. Biol. 78:359-371; El-Sherbiny et al, (2007) Cancer Research 67(18):8444-9; and Nolte-'t Hoen et al, (2007) Blood 109:670-673). Typically, NK cell cytotoxicity is determined by any assay described in the EXAMPLE. NK cell cytotoxicity may be measured by a classical in vitro chromium release test of cytotoxicity. Effector cells are typically fresh PB-NK from healthy donors. The target cells are typically the murine mastocytoma P815 cells or EBV-infected B cell lines. Accordingly, the antibody (preferably the monoclonal antibody) of the present invention is selected if it causes an increase in the reactivity or cytotoxicity of NK cells toward target cells (infected cells, tumor cells, pro-inflammatory cells, etc.), increased activation, activation markers (e.g., CD107 expression) and/or IFNgamma production in NK cells, and/or increased the frequency in vivo of such activated, reactive, cytotoxic and/or activated NK cells.

In some embodiments, the subject suffers from a cancer or an infectious disease. Accordingly, a further object of the present invention relates to a method of treating a cancer or an infectious disease in a subject in need thereof comprising administering to the subject a therapeutically effective amount of an antibody of the present invention. Preferably, according to this embodiment, the antibody of the present invention does not comprise a Fc region mediating ADCC, CDC or antibody-induced phagocytosis.

The present invention thus further relates to an antibody, a composition, a pharmaceutical composition or a medicament of the present invention for use in treating a cancer, an infectious disease or an inflammatory and/or auto-immune disease.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the present invention contemplate any one or more of these aspects of treatment. In one embodiment, the terms "treating" or "treatment" refers to both therapeutic treatment and prophylactic or preventative measures; wherein the object is to prevent or slow down (lessen) the targeted disease. Therefore, in one embodiment, those in need of treatment may include those already with the disorder as well as those prone to have the disorder or those in whom the disorder is to be prevented.

As used herein, the term "cancer" has its general meaning in the art and includes, but is not limited to, solid tumors and blood borne tumors The term cancer includes diseases of the skin, tissues, organs, bone, cartilage, blood and vessels. The term "cancer" further encompasses both primary and metastatic cancers. Examples of cancers that may treated by methods and compositions of the invention include, but are not limited to, cancer cells from the bladder, blood, bone, bone marrow, brain, breast, colon, esophagus, gastrointestinal, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; non-encapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malign melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; NK leukemia or NK lymphoma, such as for example, extranodal and non-extranodal NK/T lymphomas; NK cell derived malignancies; and acute NK leukemia; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

As used herein the term "infectious disease" includes any infection caused by viruses, bacteria, protozoa, molds or fungi. In some embodiments, the viral infection comprises infection by one or more viruses selected from the group consisting of Arenaviridae, Astroviridae, Birnaviridae, Bromoviridae, Bunyaviridae, Caliciviridae, Closteroviridae, Comoviridae, Cystoviridae, Flaviviridae, Flexiviridae, Hepevirus, Leviviridae, Luteoviridae, Mononegavirales, Mosaic Viruses, Nidovirales, Nodaviridae, Orthomyxoviridae, Picobirnavirus, Picornaviridae, Potyviridae, Reoviridae, Retroviridae, Sequiviridae, Tenuivirus, Togaviridae, Tombusviridae, Totiviridae, Tymoviridae, Hepadnaviridae, Herpesviridae, Paramyxoviridae or Papillomaviridae viruses. Relevant taxonomic families of RNA viruses include, without limitation, Astroviridae, Birnaviridae, Bromoviridae, Caliciviridae, Closteroviridae, Comoviridae, Cystoviridae, Flaviviridae, Flexiviridae, Hepevirus, Leviviridae, Luteoviridae, Mononegavirales, Mosaic Viruses, Nidovirales, Nodaviridae, Orthomyxoviridae, Picobirnavirus, Picornaviridae, Potyviridae, Reoviridae, Retroviridae, Sequiviridae, Tenuivirus, Togaviridae, Tombusviridae, Totiviridae, and Tymoviridae viruses. In some embodiments, the viral infection comprises infection by one or more viruses selected from the group consisting of adenovirus, rhinovirus, hepatitis, immunodeficiency virus, polio, measles, Ebola, Coxsackie, Rhino, West Nile, small pox, encephalitis, yellow fever, Dengue fever, influenza (including human, avian, and swine), lassa, lymphocytic choriomeningitis, junin, machuppo, guanarito, hantavirus, Rift Valley Fever, La Crosse, California encephalitis, Crimean-Congo, Marburg, Japanese Encephalitis, Kyasanur Forest, Venezuelan equine encephalitis, Eastern equine encephalitis, Western equine encephalitis, severe acute respiratory syndrome (SARS), parainfluenza, respiratory syncytial, Punta Toro, Tacaribe, pachindae viruses, adenovirus, Dengue fever, influenza A and influenza B (including human, avian, and swine), junin, measles, parainfluenza, Pichinde, punta toro, respiratory syncytial, rhinovirus, Rift Valley Fever, severe acute respiratory syndrome (SARS), Tacaribe, Venezuelan equine encephalitis, West Nile and yellow fever viruses, tick-borne encephalitis virus, Japanese encephalitis virus, St. Louis encephalitis virus, Murray Valley virus, Powassan virus, Rocio virus, louping-ill virus, Banzi virus, Ilheus virus, Kokobera virus, Kunjin virus, Alfuy virus, bovine diarrhea virus, and Kyasanur forest disease. Bacterial infections that can be treated according to this invention include, but are not limited to, infections caused by the following: *Staphylococcus; Streptococcus*, including *S. pyogenes; Enterococci; Bacillus*, including *Bacillus anthraces*, and *Lactobacillus; Listeria; Corynebacterium diphtheriae; Gardnerella* including *G. vaginalis; Nocardia; Streptomyces; Thermoactinomyces vulgaris; Treponerna; Camplyobacter, Pseudomonas* including *aeruginosa; Legionella; Neisseria* including *N. gonorrhoeae* and *N. meningitides; Flavobacterium* including *F. meningosepticum* and *F. odoraturn; Brucella; Borde-* tella including *B. pertussis* and *B. bronchiseptica*; *Escherichia* including *E. coli, Klebsiella; Enterobacter, Serratia* including *S. marcescens* and *S. liquefaciens; Edwardsiella; Proteus* including *P. mirabilis* and *P. vulgaris; Streptobacillus; Rickettsiaceae* including *R. fickettsfi, Chlamydia* including *C. psittaci* and *C. trachornatis; Mycobacterium* including *M. tuberculosis, M. intracellulare, M. folluiturn, M. laprae, M. avium, M. bovis, M. africanum, M. kansasii, M. intracellulare, and M. lepraernurium*; and *Nocardia*. Protozoa infections that may be treated according to this invention include, but are not limited to, infections caused by leishmania, kokzidioa, and trypanosoma. A complete list of infectious diseases can be found on the website of the National Center for Infectious Disease (NCID) at the Center for Disease Control (CDC) (World Wide Web (www) at cdc.gov/ncidod/diseases/), which list is incorporated herein by reference. All of said diseases are candidates for treatment using the compositions according to the invention.

Examples of inflammatory diseases include, but are not limited to, arthritis, rheumatoid arthritis, ankylosing spondylitis, osteoarthritis, psoriatic arthritis, juvenile idiopathic arthritis, juvenile rheumatoid arthritis, arthritis uratica, gout, chronic polyarthritis, periarthritis humeroscapularis, cervical arthritis, lumbosacral arthritis, enteropathic arthritis and ankylosing spondylitis, asthma, dermatitis, psoriasis, scleroderma, polymyositis, dermatomyositis, juvenila dermatomyositis, primary biliary cirrhosis, fibrosis, cystic fibrosis, pulmonary fibrosis, cirrhosis, endomyocardial fibrosis, dediastinal fibrosis, myelofibrosis, retroperitoneal fibrosis, nephrogenic fibrosis, Keloids, scleroderma, arthrofibrosis, post transplantation late and chronic solid organ rejection, multiple sclerosis, systemic lupus erythematosus, lupus nephritis, pemphigus, Pemphigus vulgaris, Pemphigus herpetiformis, Pemphigus vegetans, IgA pemphigus, Pemphigus erythematosus, bullous pemphigoid, Pemphigoid gestationis, Mucous membrane dermatosis, Pemphigoid nodularis, Linear IgA bullous dermatosis, Bullous lichen planus, Epidermolysis bullosa acquisita, autoimmune diabetes, diabetic retinopathy, diabetic nephropathy, diabetic vasculopathy, ocular inflammation, uveitis, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina, small artery disease, acute disseminated encephalomyelitis, idiopathic thrombocytopenic purpura, multiple sclerosis, systemic sclerosis, antiphospholipid syndrome, Sjoegren's syndrome, autoimmune hemolytic anemia, colitis, Crohn's Disease, ulcerative colitis, Inflammatory Bowel Disease (IBD), embolism, pulmonary embolism, arterial embolism, venous embolism, allergic inflammation, cardiovascular disease, graft-related diseases, graft versus host disease (GVHD), disorders associated with graft transplantation rejection, chronic rejection, and tissue or cell allografts or xenografts, autoimmune diseases, degeneration after trauma, stroke, transplant rejection, allergic conditions and hypersensitivity, e.g., allergic rhinitis, allergic eczema and the like, skin diseases, dermal inflammatory disorders, or any combination thereof.

Examples of autoimmune diseases include, but are not limited to, lupus (e.g., lupus erythematosus, lupus nephritis), Hashimoto's thyroiditis, Wegener's disease; primary myxedema, Graves' disease, pernicious anemia, autoimmune atrophic gastritis, Addison's disease, diabetes (e.g. insulin dependent diabetes mellitus, type I diabetes mellitus, type II diabetes mellitus), good pasture's syndrome, myasthenia gravis, pemphigus, intestinal inflammatory conditions such as Crohn's disease and ulcerative colitis; sympathetic ophthalmia, autoimmune uveitis, multiple sclerosis, autoimmune hemolytic anemia, idiopathic thrombocytopenia, primary biliary cirrhosis, chronic action hepatitis, ulcerative colitis, Sjogren's syndrome, arthritis conditions such as rheumatoid arthritis, psoriatic arthritis, ankylosing spondylitis and juvenile idiopathic arthritis; polymyositis, scleroderma, psoriasis, primary sclerosing cholangitis; asthma, transplant rejection (host versus graft disease); graft versus host disease and mixed connective tissue disease.

The present invention also provides for therapeutic applications where an antibody of the present invention is used in combination with at least one further therapeutic agent, e.g., for treating cancer. Such administration may be simultaneous, separate or sequential. For simultaneous administration the agents may be administered as one composition or as separate compositions, as appropriate. The further therapeutic agent is typically relevant for the disorder to be treated. Exemplary therapeutic agents include other anti-cancer antibodies, cytotoxic agents, chemotherapeutic agents, anti-angiogenic agents, anti-cancer immunogens, cell cycle control/apoptosis regulating agents, hormonal regulating agents, and other agents described below.

In some embodiments, the second agent is a natural ligand of an NK cell activating or an antibody that binds and activates an NK cell activating receptor other than CD160-TM. In some embodiments, the agent is an agent that increases the presence of a natural ligand of an NK cell activating receptor on the surface of a target cell (e.g., infected cells, or tumor cells). In one embodiment, the antibody of the present invention does not comprise a Fc region mediating ADCC, CDC or antibody-induced phagocytosis and is used in combination with a second agent that (i) is a natural ligand of an NK cell activating or an antibody that binds and activates an NK cell activating receptor other than CD160-TM and/or (ii) increases the presence of a natural ligand of an NK cell activating receptor on the surface of a target cell. NK cell activating receptors include, for example, NKG2D or activating MR receptors (KIR2DS receptors, KIR2DS2, KIR2DS4). As used herein, the term "activating NK receptor" refers to any molecule on the surface of NK cells that, when stimulated, causes a measurable increase in any property or activity known in the art as associated with NK activity, such as cytokine (for example IFN-γ and TNF-α) production, increases in intracellular free calcium levels, the ability to target cells in a redirected killing assay as described, e.g., elsewhere in the present specification, or the ability to stimulate NK cell proliferation. The term "activating NK receptor" includes but is not limited to activating forms or MR proteins (for example KIR2DS proteins), NKG2D, IL-2R, IL-12R, IL-15R, IL-18R and IL-21R. Examples of ligands that act as agonists at activating receptors include, e.g., IL-2, IL-15, IL-21 polypeptides. In some embodiments, the second antibody is specific for CD137. As used herein the term "CD137" has its general meaning in the art and may also be referred to as Ly63, ILA or 4-1BB. CD137 is a member of the tumor necrosis factor (TNF) receptor family. Members of this receptor family and their structurally related ligands are important regulators of a wide variety of physiologic processes and play an important role in the regulation of immune responses. CD137 is expressed by activated NK cells, T and B lymphocytes and monocytes/macrophages. The gene encodes a 255-amino acid protein with 3 cysteine-rich motifs in the extracellular domain (characteristic of this receptor family), a transmembrane region, and a short N-terminal cytoplasmic portion containing potential phosphorylation sites. Expression in primary cells is strictly activation dependent. The ligand for the receptor is TNFSF9. Human CD137 is reported to bind only to its ligand. Agonists include the native ligand (TNFSF9), aptamers (see McNamara et al. (2008) J. Clin. Invest. 1 18: 376-386), and antibodies.

In some embodiments, antibody of the present invention is used in combination with a second antibody which induces, via ADCC, the death of a cell expressing an antigen to which the second antibody binds. In one embodiment, the antibody of the present invention does not comprise a Fc region mediating ADCC, CDC or antibody-induced phagocytosis and is used in combination with a second agent which induces, via ADCC, the death of a cell expressing an antigen to which the second antibody binds. In one embodiment, the antibody of the invention is conjugated to a second antibody which induces, via ADCC, the death of a cell expressing an antigen to which the second antibody binds. NK cells have an important role in inducing ADCC and increased reactivity of NK cells can be directed to target cells through use of such a second agent. In some embodiments, the second agent is an antibody specific for a cell surface antigens, e.g., membrane antigens. In some embodiments, the second antibody is specific for a tumor antigen as described herein (e.g., molecules specifically expressed by tumor cells), such as CD20, CD52, ErbB2 (or HER2/Neu), CD33, CD22, CD25, MUC-1, CEA, KDR, $\alpha V\beta 3$, etc., particularly lymphoma antigens (e.g., CD20). Accordingly, the present invention also provides methods to enhance the anti-tumor effect of monoclonal antibodies directed against tumor antigen(s). In the methods of the invention, ADCC function is specifically augmented, which in turn enhances target cell killing, by sequential administration of an antibody directed against one or more tumor antigens, and an antibody of the present invention.

Accordingly, a further object relates to a method of enhancing NK cell antibody-dependent cellular cytotoxicity (ADCC) of an antibody in a subject in need thereof comprising administering to the subject the antibody, and administering to the subject an antibody of the present invention, wherein preferably the antibody of the present invention does not comprise a Fc region mediating ADCC, CDC or antibody-induced phagocytosis.

A further object of the present invention relates to a method of treating cancer in a subject in need thereof comprising administering to the subject a first antibody selective for a cancer cell antigen, and administering to the subject an antibody of the present invention, wherein preferably the antibody of the present invention does not comprise a Fc region mediating ADCC, CDC or antibody-induced phagocytosis.

A number of antibodies are currently in clinical use for the treatment of cancer, and others are in varying stages of clinical development. Antibodies of interest for the methods of the invention act through ADCC, and are typically selective for tumor cells, although one of skill in the art will recognize that some clinically useful antibodies do act on non-tumor cells, e.g., CD20. There are a number of antigens and corresponding monoclonal antibodies for the treatment of B cell malignancies. One popular target antigen is CD20, which is found on B cell malignancies. Rituximab is a chimeric unconjugated monoclonal antibody directed at the CD20 antigen. CD20 has an important functional role in B cell activation, proliferation, and differentiation. The CD52 antigen is targeted by the monoclonal antibody alemtuzumab, which is indicated for treatment of chronic lymphocytic leukemia. CD22 is targeted by a number of antibodies, and has recently demonstrated efficacy combined with toxin in chemotherapy-resistant hairy cell leukemia. Monoclonal antibodies targeting CD20, also include tositumomab and ibritumomab. Monoclonal antibodies useful in the methods of the invention, which have been used in solid tumors, include without limitation edrecolomab and trastuzumab (herceptin). Edrecolomab targets the 17-1 A antigen seen in colon and rectal cancer, and has been approved for use in Europe for these indications. Its antitumor effects are mediated through ADCC, CDC, and the induction of an anti-idiotypic network. Trastuzumab targets the HER-2/neu antigen. This antigen is seen on 25% to 35% of breast cancers. Trastuzumab is thought to work in a variety of ways: downregulation of HER-2 receptor expression, inhibition of proliferation of human tumor cells that overexpress HER-2 protein, enhancing immune recruitment and ADCC against tumor cells that overexpress HER-2 protein, and downregulation of angiogenesis factors. Alemtuzumab (Campath) is used in the treatment of chronic lymphocytic leukemia; colon cancer and lung cancer; Gemtuzumab (Mylotarg) finds use in the treatment of acute myelogenous leukemia; Ibritumomab (Zevalin) finds use in the treatment of non-Hodgkin's lymphoma; Panitumumab (Vectibix) finds use in the treatment of colon cancer. Cetuximab (Erbitux) is also of interest for use in the methods of the invention. The antibody binds to the EGF receptor (EGFR), and has been used in the treatment of solid tumors including colon cancer and squamous cell carcinoma of the head and neck (SCCHN).

In one embodiment, the antibody (preferably the monoclonal antibody) of the present invention is used in combination with at least one immune checkpoint inhibitor (ICI). Various tumors are able to express molecular factors protecting them from being attacked by the immune system, and are thus capable of successfully escaping the immune system supervision control. This "tumor immune escape" is mainly due to the antagonistic blocking of receptors and binding sites targeted by immune cell ligands. Immune checkpoint inhibitors are molecules especially targeting this kind of inhibitory mechanisms developed by tumorous cells. Examples of ICIs include, but are not limited to, inhibitors of CTLA-4 (such as, for example, ipilumab and tremelimumab), inhibitors of PD-1 (such as, for example, pembrolizumab, pidilizumab, nivolumab and AMP-224) inhibitors of PD-L1 (such as, for example, atezolizumab, avelumab, durvalumab and BMS-936559), inhibitors of LAG3 (such as, for example, IMP321) and inhibitors of B7-H3 (such as, for example, MGA271). In one embodiment, the antibody of the present invention does not comprise a Fc region mediating ADCC, CDC or antibody-induced phagocytosis and is used in combination with at least one immune checkpoint inhibitor (ICI).

In one embodiment, the antibody (preferably the monoclonal antibody) of the present invention inhibits the binding of CD160-TM to one of its ligands, such as, for example, to MHC class I molecules. As used herein, the term "ligand" refers to a member of a pair ligand/receptor, and binds to the other member of the pair. Inhibiting the binding of CD160-TM to one of its ligands may thus inhibit the functionality of NK cells expressing CD160-TM.

Such inhibition may be useful for treating Paroxysmal Nocturnal Hemoglobinuria or an inflammatory and/or autoimmune disease. Examples of inflammatory and/or autoimmune disease are listed hereinabove.

A further object of the present invention thus relates to a method of treating Paroxysmal Nocturnal Hemoglobinuria in a subject in need thereof comprising administering to the subject a therapeutically effective amount of the antibody (preferably the monoclonal antibody) of the present invention. As used herein, the term "Paroxysmal Nocturnal Hemoglobinuria" or "PNH" has its general meaning in the art and refers to an acquired clonal hematopoietic stem cell disorder characterized by corpuscular hemolytic anemia, bone marrow failure and frequent thrombotic events. In some embodiments, the subject is not mutated for the PIGA gene (phosphatidylinositol glycan anchor biosynthesis class A, Gene ID: 5277).

The present invention thus further relates to an antibody, a composition, a pharmaceutical composition or a medicament for use in the treatment of PNH.

In one embodiment, when used in the treatment of PNH, the antibody (preferably the monoclonal antibody) of the present invention does not comprise a Fc region mediating ADCC, CDC or antibody-induced phagocytosis. In one embodiment, when used in the treatment of PNH, the antibody (preferably the monoclonal antibody) of the present invention consists of or comprises a Fab, Fab', Fab'-SH, F(ab')$_2$, Fv, a diabody, single-chain antibody fragment, or a multispecific antibody comprising multiple different antibody fragments. Preferably, according to this embodiment, the antibody (preferably the monoclonal antibody) of the present invention is a Fab.

The present invention further relates to a fusion protein comprising an antibody (preferably a monoclonal antibody) of the present invention.

In some embodiments, the antibody (preferably the monoclonal antibody) of the present invention is conjugated to a therapeutic moiety, i.e., a drug. The therapeutic moiety can be, e.g., a cytotoxin, a chemotherapeutic agent, a cytokine, an immunosuppressant, an immune stimulator, a lytic peptide, or a radioisotope. Such conjugates are referred to herein as an "antibody-drug conjugates" or "ADCs". In one embodiment, the antibody of the present invention does not comprise a Fc region mediating ADCC, CDC or antibody-induced phagocytosis and is conjugated to a therapeutic moiety.

In some embodiments, the antibody (preferably the monoclonal antibody) of the present invention is conjugated to a cytotoxic moiety. In one embodiment, the antibody of the present invention does not comprise a Fc region mediating ADCC, CDC or antibody-induced phagocytosis and is conjugated to a cytotoxic moiety.The cytotoxic moiety may, for example, be selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor such as maytansine or an analog or derivative thereof; an antimitotic agent such as monomethyl auristatin E or F or an analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C; a platinum derivative such as cisplatin or carboplatin; duocarmycin A, duocarmycin SA, rachelmycin (CC-1065), or an analog or derivative thereof; an antibiotic such as dactinomycin, bleomycin, daunorubicin, doxorubicin, idarubicin, mithramycin, mitomycin, mitoxantrone, plicamycin, anthramycin (AMC)); pyrrolo[2,1-c][1,4]-benzodiazepines (PDB); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, Pseudomonas exotoxin, alorin, saporin, modeccin, gelanin, abrin A chain, modeccin A chain, alpha-sarcin, Aleurites fordii proteins, dianthin proteins, Phytolacca americana proteins such as PAPI, PAPII, and PAP-S, Momordica charantia inhibitor, curcin, crotin, Sapaonaria officinalis inhibitor, gelonin, mitogellin, restrictocin, phenomycin, and enomycin toxins; ribonuclease (RNase); DNase I, Staphylococcal enterotoxin A; pokeweed antiviral protein; diphtherin toxin; and Pseudomonas endotoxin.

In some embodiments, the antibody (preferably the monoclonal antibody) of the present invention is conjugated to an auristatin or a peptide analog, derivative or prodrug thereof. In one embodiment, the antibody of the present invention does not comprise a Fc region mediating ADCC, CDC or antibody-induced phagocytosis and is conjugated to an auristatin or a peptide analog, derivative or prodrug thereof. Auristatins have been shown to interfere with microtubule dynamics, GTP hydrolysis and nuclear and cellular division (Woyke et al (2001) Antimicrob. Agents and Chemother. 45(12): 3580-3584) and have anti-cancer (U.S. Pat. No. 5,663,149) and antifungal activity (Pettit et al., (1998) Antimicrob. Agents and Chemother. 42: 2961-2965. For example, auristatin E can be reacted with para-acetyl benzoic acid or benzoylvaleric acid to produce AEB and AEVB, respectively. Other typical auristatin derivatives include AFP, MMAF (monomethyl auristatin F), and MMAE (monomethyl auristatin E). Suitable auristatins and auristatin analogs, derivatives and prodrugs, as well as suitable linkers for conjugation of auristatins to Abs, are described in, e.g., U.S. Pat. Nos. 5,635,483, 5,780,588 and 6,214,345 and in International patent application publications WO02088172, WO2004010957, WO2005081711, WO2005084390, WO2006132670, WO03026577, WO200700860, WO207011968 and WO205082023.

In some embodiments, the antibody (preferably the monoclonal antibody) of the present invention is conjugated to pyrrolo[2,1-c][1,4]-benzodiazepine (PDB) or an analog, derivative or prodrug thereof. In one embodiment, the antibody of the present invention does not comprise a Fc region mediating ADCC, CDC or antibody-induced phagocytosis and is conjugated to a PDB or an analog, derivative or prodrug thereof. Suitable PDBs and PDB derivatives, and related technologies are described in, e.g., Hartley J. A. et al., Cancer Res 2010; 70(17) : 6849-6858; Antonow D. et al., Cancer J 2008; 14(3) : 154-169; Howard P. W. et al., Bioorg Med Chem Lett 2009; 19: 6463-6466 and Sagnou et al., Bioorg Med Chem Lett 2000; 10(18) : 2083-2086.

In some embodiments, the antibody (preferably the monoclonal antibody) of the present invention is conjugated to a cytotoxic moiety selected from the group consisting of an anthracycline, maytansine, calicheamicin, duocarmycin, rachelmycin (CC-1065), dolastatin 10, dolastatin 15, irinotecan, monomethyl auristatin E, monomethyl auristatin F, a PDB, or an analog, derivative, or prodrug of any thereof. In one embodiment, the antibody of the present invention does not comprise a Fc region mediating ADCC, CDC or antibody-induced phagocytosis and is conjugated to a cytotoxic moiety selected from the group consisting of an anthracycline, maytansine, calicheamicin, duocarmycin, rachelmycin (CC-1065), dolastatin 10, dolastatin 15, irinotecan, monomethyl auristatin E, monomethyl auristatin F, a PDB, or an analog, derivative, or prodrug of any thereof.

In some embodiments, the antibody (preferably the monoclonal antibody) of the present invention is conjugated to an anthracycline or an analog, derivative or prodrug thereof. In some embodiments, the antibody is conjugated to maytansine or an analog, derivative or prodrug thereof. In some embodiments, the antibody is conjugated to calicheamicin or an analog, derivative or prodrug thereof. In some embodiments, the antibody is conjugated to duocarmycin or an analog, derivative or prodrug thereof. In some embodiments, the antibody is conjugated to rachelmycin (CC-1065) or an analog, derivative or prodrug thereof. In some embodiments, the antibody is conjugated to dolastatin 10 or an analog, derivative or prodrug thereof. In some embodiments, the antibody is conjugated to dolastatin 15 or an analog, derivative or prodrug thereof. In some embodiments, the antibody is conjugated to monomethyl auristatin E or an analog, derivative or prodrug thereof. In some embodiments, the antibody is conjugated to monomethyl auristatin F or an analog, derivative or prodrug thereof. In some embodiments, the antibody is conjugated to pyrrolo[2,1-c][1,4]-benzodiazepine or an analog, derivative or prodrug thereof. In some embodiments, the antibody is conjugated to irinotecan or an analog, derivative or prodrug thereof.

Techniques for conjugating molecule to antibodies, are well-known in the art (See, e.g., Amon et al., "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al., "Antibodies For Drug Delivery," in Controlled Drug Delivery (Robinson et al. eds., Marcel Deiker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al., 1982, Immunol. Rev. 62:119-58. See also, e.g., PCT publication WO 89/12624.) Typically, the nucleic acid molecule is covalently attached to lysines or cysteines on the antibody, through N-hydroxysuccinimide ester or maleimide functionality respectively. Methods of conjugation using engineered cysteines or incorporation of unnatural amino acids have been reported to improve the homogeneity of the conjugate (Axup, J. Y., Bajjuri, K. M., Ritland, M., Hutchins, B. M., Kim, C. H., Kazane, S. A., Halder, R., Forsyth, J. S., Santidrian, A. F., Stafin, K., et al. (2012). Synthesis of site-specific antibody-drug conjugates using unnatural amino acids. Proc. Natl. Acad. Sci. USA 109, 16101-16106.; Junutula, J. R., Flagella, K. M., Graham, R. A., Parsons, K. L., Ha, E., Raab, H., Bhakta, S., Nguyen, T., Dugger, D. L., Li, G., et al. (2010). Engineered thio-trastuzumab-DM1 conjugate with an improved therapeutic index to target humanepidermal growth factor receptor 2-positive breast cancer. Clin. Cancer Res.16, 4769-4778.). Junutula et al. (2008) developed cysteine-based site-specific conjugation called "THIOMABs" (TDCs) that are claimed to display an improved therapeutic index as compared to conventional conjugation methods. Conjugation to unnatural amino acids that have been incorporated into the antibody is also being explored for ADCs; however, the generality of this approach is yet to be established (Axup et al., 2012). In particular the one skilled in the art can also envisage Fc-containing polypeptide engineered with an acyl donor glutamine-containing tag (e.g., Gln-containing peptide tags or Q-tags) or an endogenous glutamine that are made reactive by polypeptide engineering (e.g., via amino acid deletion, insertion, substitution, or mutation on the polypeptide). Then a transglutaminase, can covalently cross-link with an amine donor agent (e.g., a small molecule comprising or attached to a reactive amine) to form a stable and homogenous population of an engineered Fc-containing polypeptide conjugate with the amine donor agent being site-specifically conjugated to the Fc-containing polypeptide through the acyl donor glutamine-containing tag or the accessible/exposed/reactive endogenous glutamine (WO 2012059882).

As used herein, the term "therapeutically effective amount" refers to an amount effective, at dosages and for periods of time necessary, to achieve a desired therapeutic result. Thus, the terms "therapeutically effective amount" may mean a level or amount of antibodies that is aimed at, without causing significant negative or adverse side effects to the target, (1) delaying or preventing the onset of the targeted disease; (2) slowing down or stopping the progression, aggravation, or deterioration of one or more symptoms of the targeted disease; (3) bringing about ameliorations of the symptoms of the targeted disease; (4) reducing the severity or incidence of the targeted disease; or (5) curing the targeted disease. A therapeutically effective amount may be administered prior to the onset of the targeted disease, for a prophylactic or preventive action. Alternatively, or additionally, the therapeutically effective amount may be administered after initiation of the targeted disease, for a therapeutic action.

A therapeutically effective amount of the antibody (preferably the monoclonal antibody) of the present invention may vary according to factors such as the disease state, age, sex, and weight of the individual, and the ability of the antibody (preferably the monoclonal antibody) of the present invention to elicit a desired response in the individual. A therapeutically effective amount is also one in which any toxic or detrimental effects of the antibody or antibody portion are outweighed by the therapeutically beneficial effects. The efficient dosages and dosage regimens for the antibody (preferably the monoclonal antibody) of the present invention depend on the disease or condition to be treated and may be determined by the persons skilled in the art. A physician having ordinary skill in the art may readily determine and prescribe the effective amount of the pharmaceutical composition required. For example, the physician could start doses of the antibody (preferably the monoclonal antibody) of the present invention employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. Typically, the ability of a compound to inhibit cancer may, for example, be evaluated in an animal model system predictive of efficacy in human tumors. Alternatively, this property of a composition may be evaluated by examining the ability of the compound to induce cytotoxicity by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected. An exemplary, non-limiting range for a therapeutically effective amount of an antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an antibody of the present invention is 0.02-100 mg/kg, such as about 0.02-30 mg/kg, such as about 0.05-10 mg/kg or 0.1-3 mg/kg, for example about 0.5-2 mg/kg. Administration may e.g., be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g., at predefined points in time. In some embodiments, the efficacy may be monitored by visualization of the disease area, or by other diagnostic methods described further herein, e.g., by performing one or more PET-CT scans, for example using a labeled antibody of the present invention, fragment or mini-antibody derived from the antibody (preferably the monoclonal antibody) of the present invention. If desired, an effective daily dose of a pharmaceutical composition may be administered as two, three, four, five, six or more sub-doses administered separately at appropriate intervals throughout the day, optionally, in unit dosage forms. In some embodiments, the human antibody (preferably the monoclonal antibody) of the present invention are administered by slow continuous infusion over a long period, such as more than 24 hours, in order to minimize any unwanted side effects. An effective dose of an antibody of the present invention may also be administered using a weekly, biweekly or triweekly dosing period. The dosing period may be restricted to, e.g., 8 weeks, 12 weeks or until clinical progression has been established. As non-limiting examples, treatment according to the present invention may be provided as a daily dosage of an antibody of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Typically, the antibody (preferably the monoclonal antibody) of the present invention is administered to the subject in the form of a pharmaceutical composition which comprises a pharmaceutically acceptable carrier.

The term "pharmaceutically acceptable carrier" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a patient, the composition will be formulated for administration to the patient. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 mg/m$^2$ and 500 mg/m$^2$. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition of the invention for injection (e.g., intramuscular, i.v.) could be prepared to contain sterile buffered water (e.g., 1 ml for intramuscular), and between about 1 ng to about 100 mg, e.g., about 50 ng to about 30 mg or more preferably, about 5 mg to about 25 mg, of an anti-CD160-TM antibody of the invention.

Another object of the invention is the use of at least one antibody of the present invention for detecting CD160-TM in a sample, preferably in a biological sample, in vitro or in vivo. Another object of the invention is the use of at least one antibody of the present invention for detecting activated NK cells in a sample, preferably in a biological sample, in vitro or in vivo. Examples of assays in which the antibody of the invention may be used, include, but are not limited to, ELISA, sandwich ELISA, RIA, FACS, tissue immunohistochemistry, Western-blot, and immunoprecipitation.

Another object of the invention is a method for detecting CD160-TM in a sample, comprising contacting the sample with an antibody of the invention and detecting the antibody bound to CD160-TM, thereby indicating the presence of CD160-TM in the sample. Another object of the invention is a method for detecting activated NK cells in a sample, comprising contacting the sample with an antibody of the invention and detecting the antibody bound to CD160-TM, thereby indicating the presence of activated NK cells in the sample.

In one embodiment of the invention, the sample is a biological sample. Examples of biological samples include, but are not limited to, tissue lysates and extracts prepared from diseased tissues, bodily fluids, preferably blood, more preferably blood serum, plasma, synovial fluid, bronchoalveolar lavage fluid, sputum, lymph, ascitic fluids, urine, amniotic fluid, peritoneal fluid, cerebrospinal fluid, pleural fluid, pericardial fluid, and alveolar macrophages.

In one embodiment of the invention, the term "sample" is intended to mean a sample taken from an individual prior to any analysis.

In one embodiment of the invention, the antibody of the invention is directly labeled with a detectable label and may be detected directly. In another embodiment, the antibody of the invention is unlabeled (and is referred as the first/primary antibody) and a secondary antibody or other molecule that can bind the anti-CD160-TM antibody is labeled. As it is well known in the art, a secondary antibody is chosen to be able to specifically bind the specific species and class of the primary antibody.

The presence of anti-CD160-TM antibody/CD160 complex in the sample can be detected and measured by detecting the presence of the labeled secondary antibody. For example, after washing away unbound secondary antibody from a well comprising the primary antibody/antigen complex or from a membrane (such as a nitrocellulose or nylon membrane) comprising the complex, the bound secondary antibody can be developed and detected based on chemiluminescence of the label for example.

Labels for the anti-CD160-TM antibody or the secondary antibody include, but are not limited to, various enzymes, prosthetic groups, fluorescent materials, luminescent materials, magnetic agents and radioactive materials. Examples of such enzymes include but are not limited to, horseradish peroxidase, alkaline phosphatase, beta-galactosidase or acetylcholinesterase; examples of prosthetic group complexes include but are not limited to, streptavidin/biotin and avidin/biotin; examples of fluorescent materials include but are not limited to, umbelliferone, fluorescein, fluorescein isothiocyanate, rhodamine, dichlorotriazinylamine fluorescein, dansyne chloride or phycoerythrin; examples of luminescent material include but are not limited to, luminal; examples of magnetic agents include gadolinium; and examples of suitable radioactive material include 125I, 131I, 35S or 3H.

Another object of the invention is an in vitro method for depleting a cell sample or a cell population from CD160-TM expressing cells (e.g., from activated NK cells), comprising contacting the cell sample with an antibody of the present invention.

Another object of the invention is an in vitro method for isolating CD160-TM expressing cells (e.g., from activated NK cells) from a cell sample or a cell population, comprising contacting the cell sample with an antibody of the present invention.

Another object of the invention is an in vitro method for activating NK cells, comprising contacting NK cells with an antibody of the present invention.

Another object of the invention is a kit comprising at least one anti-CD160-TM antibody of the invention, preferably a monoclonal anti-CD160-TM antibody.

By "kit" is intended any manufacture (e.g., a package or a container) comprising at least one reagent, preferably an antibody, for specifically detecting the expression of CD160-TM.

The kit may be promoted, distributed, or sold as a unit for performing the methods of the present invention. Furthermore, any or all of the kit reagents may be provided within containers that protect them from the external environment, such as in sealed containers.

The kits may also contain a package insert describing the kit and methods for its use.

The invention will be further illustrated by the following figures and examples. However, these examples and figures should not be interpreted in any way as limiting the scope of the present invention.

FIGURES

FIG. 1: Binding specificity of A12 and B6 antibodies on CD160-GPI vs CD160TM expressing cells. CHO or HEK cells forced to express CD160-GPI or CD160TM isoform, respectively, were labelled with the CL1-R2 monoclonal antibody or BY55 antibody (both specific for CD160-GPI) or A12 or B6 antibodies (white histograms). Mouse or human isotype control Igs were used as negative controls (black histograms). Bound antibodies were revealed with the appropriate PE-conjugated secondary reagents.

Figure 2:
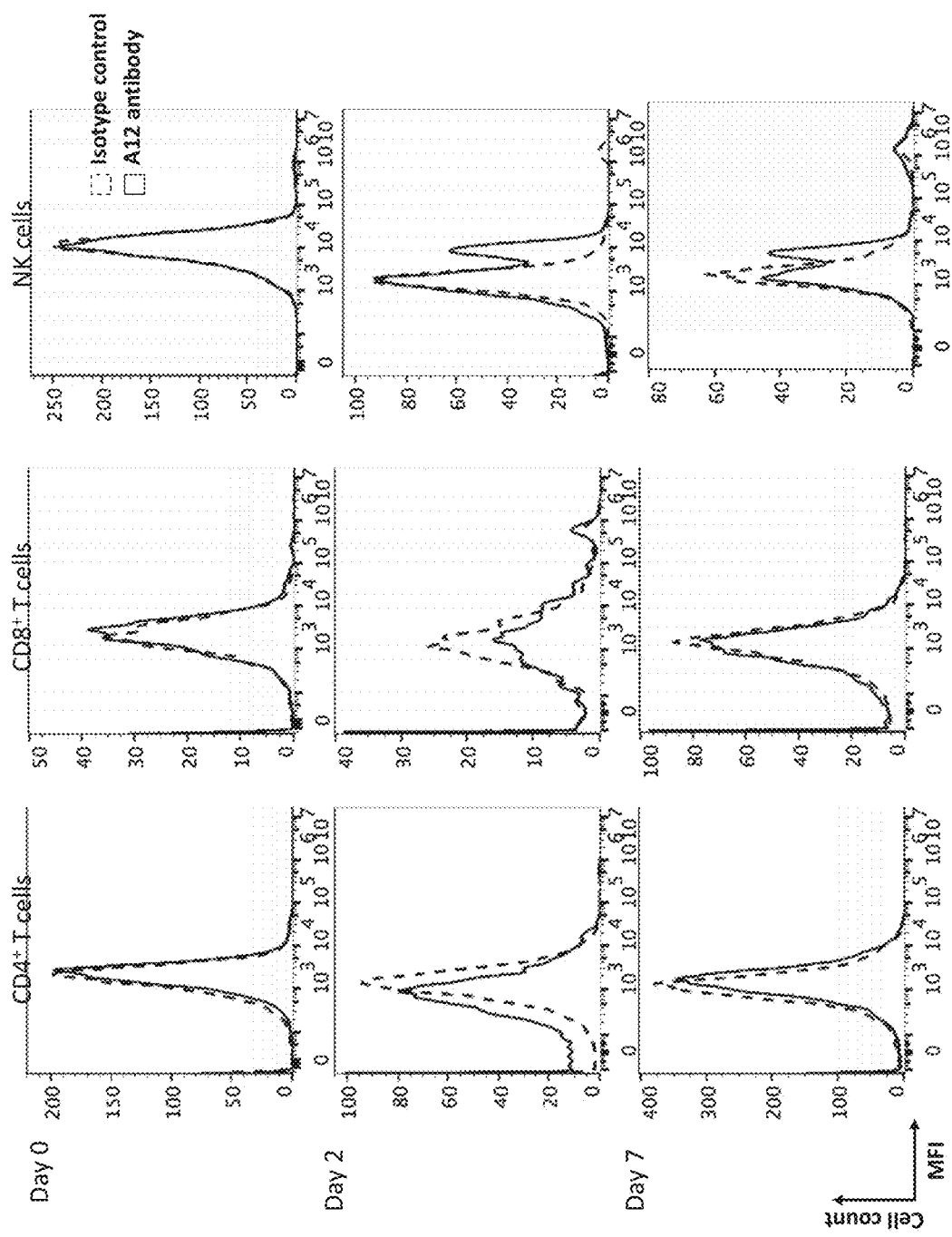

FIG. 2: Binding specificity of A12 on IL2-treated human PBMC. PBMC were either left untreated (Day 0) or incubated with IL2. Immuno-labelling were performed at the indicated time points with either an isotypic contral IgG (black histogram) or A12 antibody (grey histogram) plus PE-coupled goat anti-human IgG antibodies. Lymphocytes subsets were further identified by addition of a mix of CD8-FITC, CD56-PCS, CD3-APC and CD4-PC7 mAbs. Shown are the labellings obtained on each gated lymphocyte population.

Figure 3:
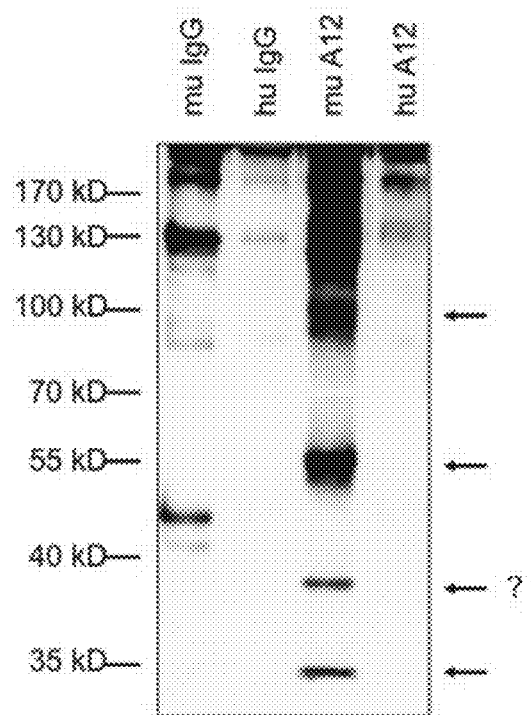

FIG. 3: Assessment of A12 specificity by immunoprecipitation. Post-nuclear lysates were prepared from HEK-CD160TM cells and subjected to immunoprecipitation with either mouse (mu IgG) or human (hu Ig) isotypic control IgG, chimeric murine A12 (mu A12) or fully human A12 (hu A12) antibody. Immuno-precipitated proteins were separated by SDS-10% PAGE under non-reducing conditions, transferred on nitrocellulose and revealed by Western blot using an anti-Flag mAb. Arrows indicate CD160TM-related signals.

Figure 4:
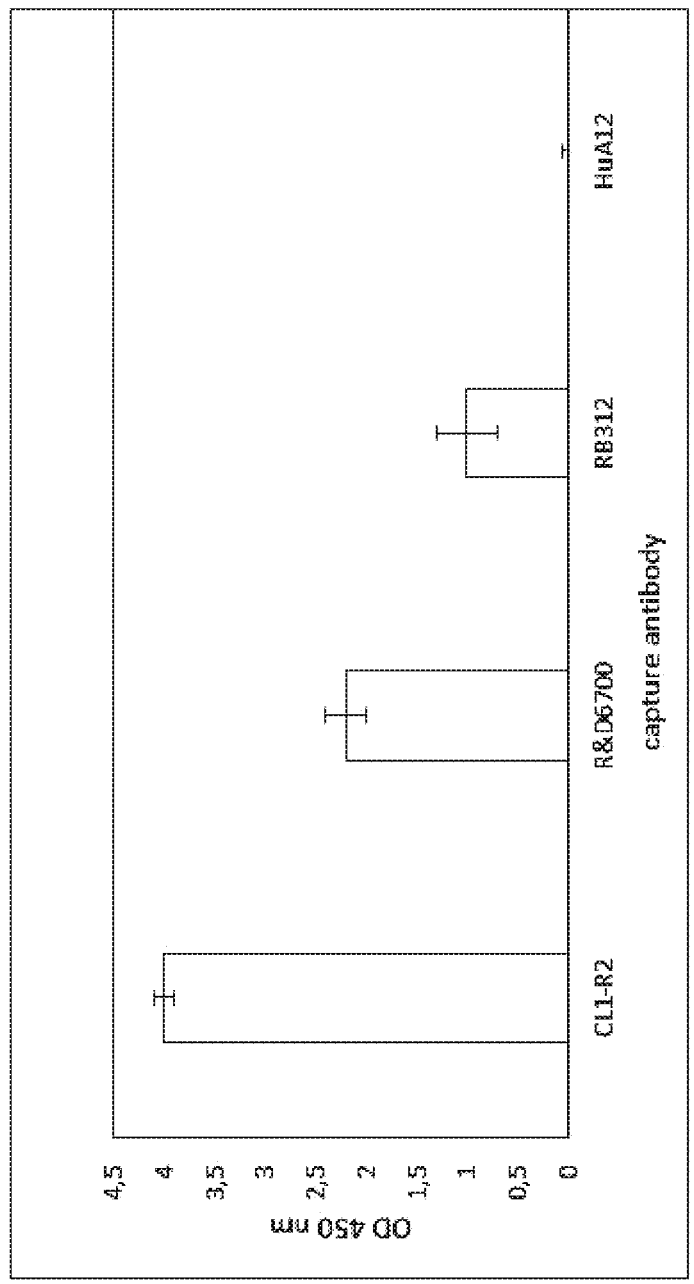

FIG. 4: sCD160 is recognized by the antibodies CL1-R2, R&D 6700 and RB312 but not A12. 1 ug per well of antibody was coated overnight on a 96 well maxisorb plate. After saturation with PBS-5% BSA, 10ng of recombinant soluble CD160-His Tag were added to each well and incubated 2h at room temperature. After washing, revelation was done with anti-His-HRP then TMB substrate. Experimental conditions were performed in triplicate and results displayed for each antibody were obtained after subtraction of the respective OD Ig control (OD=OD capture antibody−OD respective Ig control).

FIG. 5 shows the alignments of VH and VL sequences of A12 and B6 antibodies.

Figure 6:
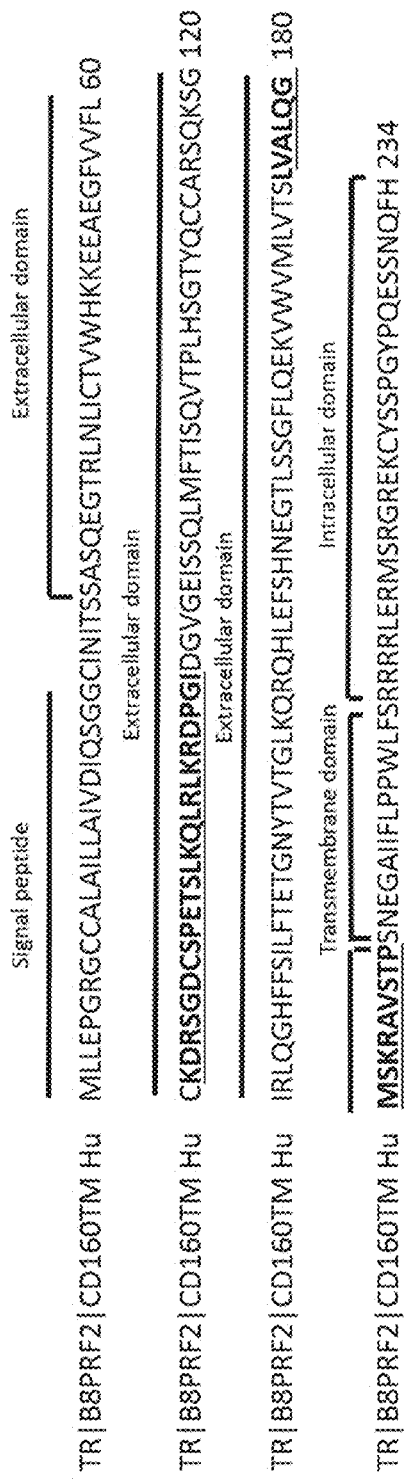

FIG. 6 shows the conformation epitope recognized A12 and B6 antibodies composes of 2 peptides. The peptides are indicated in BOLD and UNDERLINED. The different domain of the CD160-TM isoform are also represented.

Figure 7A:
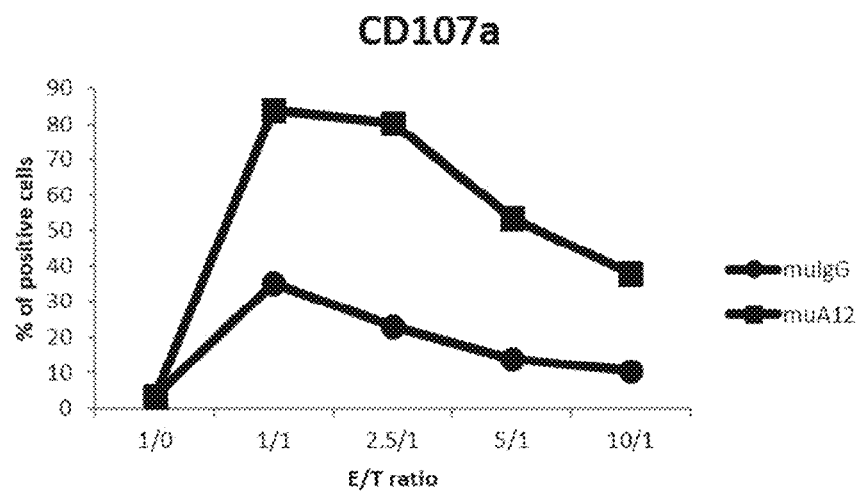
Figure 7B:
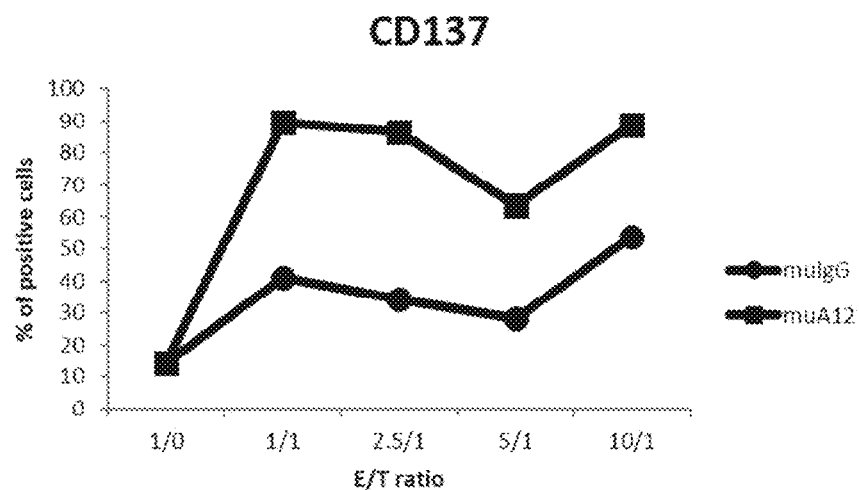

FIGS. 7A-7B: A12 induces NK cells degranulation and activation. The NK92 cell line was pre-incubated with isotype control muIgG or a chimeric Fc murine version of the human A12 antibody (muA12) plus rabbit anti-mouse IgG antibodies. Effector cells were then incubated in the presence of the NK sensible target cells (K562 cell line) at the indicated E/T ratio. The NK cell line NK92 cell degranulation and activation was monitored by detection of membrane associated CD107a (FIG. 7A) and CD137 (FIG. 7B), respectively. Given are the percentages of positive cells pre-treated with muIgG control (circles) or muA12 (squares).

EXAMPLE 1

Characterization of A12 Antibody

Material & Methods

Cells

CHO or HEK cells were transfected with a eukaryotic expression vector encompassing CD160-GPI or Flag-tagged CD160-TM cDNA, respectively. Stable transfectants were obtained by selection with the appropriate antibiotic and named thereafter CHO-CD160-GPI and HEK-CD160TM. Proper expression of CD160 isoforms was assessed by flow cytometry using the anti-CD160-GPI specific mAb CL1R2 or anti-Flag mAb plus PE-coupled goat anti-mouse IgG.

PBMC were obtained by gradient density from healthy volunteers venous blood. Activation was achieved by addition of recombinant human IL2 (100 U/ml).

Selection of A12 fully human antibody

Fully human aglycosylated anti-CD160TM antibodies were selected by phage display on HEK-CD160TM cells. Among the obtained antibodies, A12 was identified as the one giving the best recognition profile on HEK-CD160TM cells by flow cytometry. A murine chimeric version of A12 antibody, where the human IgG1 Fc portion was exchanged for a murine IgG2a Fc fragment, was also generated.

Flow Cytometry

CHO and HEK transfected cells were labelled with the anti-CD160-GPI mAb CL1-R2 or BY55, the fully human A12 or B6 antibody or their corresponding isotypic control IgG. Bound antibodies were further revealed by addition of PE-coupled goat anti-mouse or anti-human IgG. Cell acquisition was performed on a CytoFlex cytometer and results were analysed with FlowJo software.

For PBMC, CD160 labelling was performed as above. Following washes and addition of normal mouse serum, cells were incubated with a mix of CD8-FITC, CD56-PCS, CD3-APC and CD4-PC7 mAbs. After cell acquisition, analyses were performed to distinguish the $CD3^+CD4^+$ and $CD3^+CD8^+$ T lymphocytes, and the $CD3^-CD56^+$ NK cells within the lymphocytes population.

Immuno-Precipitation and Western Blot

HEK-CD160TM cells, that express a Flag-tagged version of CD160TM isoform, were lysed in 1% NP40 lysis buffer. Post-nuclear lysates were prepared and subjected to immuno-precipitation with the fully human A12 antibody or mouse chimeric A12. Human and mouse IgG were used as negative controls, respectively. Immune complexes were further collected with protein G Sepharose beads. Following washes, non-reducing sample buffer (devoid of reducing agent) was added and samples were finally heat-denatured. Proteins were separated by SDS-10% PAGE, electrically transferred on a nitrocellulose membrane and subjected to immuno-blotting with and anti-Flag mAb plus HRP-coupled goat anti-mouse IgGs. Revelation was performed by enhanced chemiluminescence and images acquired with an ImageQuant LAS device.

Results

After selection on HEK-CD160TM cells, A12 and B6 specificity for CD160TM isoform was first verified by flow cytometry on both CD160-GPI and CD160TM expressing transfectants. As shown on FIG. 1, a positive labelling was obtained with A12 and B6 antibodies on HEK-CD160TM cells but not on CHO-CD160-GPI cells. Conversely, the anti-CD160-GPI mAb CL1-R2 or BY55 gave a positive labelling only on CD160-GPI-expressing cells, ruling out the possibility that A12 and B6 negativity was linked to the non-expression of CD160-GPI on CHO transfectants.

To further confirm A12 specificity for CD160TM isoform, immuno-labelling were performed on human PBMC. Because CD160TM main feature is its unique expression on NK cells when activated, flow cytometry analyses were performed on untreated or IL2-activated cells. The corresponding results showed no recognition of the CD4+ and CD8+ T cells by A12 even at the latest activation points (FIG. 2). In contrast a positive signal was detected on part of the NK cell population 2 days after the beginning of the activation that remained visible up to 15 days. Thus A12 antibody fulfilled the characteristics for being a specific CD160TM antibody.

The ability of A12 antibody to recognize CD160TM was additionally tested by performing immuno-precipitation experiments. To this aim HEK-CD160TM cells, that expressed a Flag-tagged CD160TM receptor, were lysed and subjected to immuno-precipitation with either the fully human A12 antibody or its chimeric murine counterpart. Human or mouse IgG were used as negative controls. Immune complexes were separated by gel electrophoresis under non-reducing conditions to allow detection of CD160TM according to its multimerization state. Proteins revelation by Western blot with an anti-Flag mAb showed no specific signal in the immuno-precipitate performed with the fully human A12 when compared to control human IgG, suggesting that the antibody was unable to recognize CD160TM when partially denatured (FIG. 3). In contrast, the use of the murine chimeric A12 antibody led to the detection of proteins bands with an apparent molecular weight of 34-38, 56 and 100 kDa, that most likely correspond to the mono-, di-, and quadrimeric form of the receptor, respectively. Finally we show that A12 does not recognize the CD160 soluble isoform contrary to the antibody of the closest prior art, namely the RB312 described in Giustiniani J. et al. (Curr Mol Med. 2012 February; 12(2): 188-98, see FIG. 4). Same results were obtained with the B6 antibody (data not shown).

EXAMPLE 2

Characterization Of B6 Antibody

B6 antibody also results from the phage display selection as described in EXAMPLE 1. B6 was identified as giving a very good recognition profile on HEK-CD160TM cells by flow cytometry. A murine chimeric version of B6 antibody, where the human IgG1 Fc portion was exchanged for a murine IgG2a Fc fragment, was also generated. FIG. 5 shows the alignment of the VH and VL sequences of A12 and B6 antibodies and we can conclude that B6 is very similar to A12.

EXAMPLE 3

Characterization of the Epitope Recognized by A12 AND B6

Epitope mapping of A12 and B6 was performed according to published protocols (Sloostra et al, Mol. Divers. (1996), Timmerman et al, J. Mol. Recognit. 20 5J:283-299 (2007)). Briefly, the binding of antibody to each peptide was tested in a PEPSCAN-based ELISA. Surprisingly, we found that the epitope recognized by A12 an B6 antibodies is a conformational epitope composed of 2 peptides: SEQ ID NO: 4 and SEQ ID NO: 5. Despite the fact that the first peptide is commonly shared by CD160-GPI and CD160TM, the second peptide is specific to CD160TM explaining the specificity of both B6 and A12 antibodies for the CD160-TM isoform.

EXAMPLE 4

NK Cell Activation and CD107a Analysis Methods

The blood derived human chronic myelogenous leukemia cell line K562 (target cells) and the NK cell lymphoma derived NK92 cell line (Effector cells) growth in complete RPMI 1640 (10% FCS, 2% glutamine, 1% antibiotics) and for NK92 cell line supplemented with IL-2 (200 UI/ml).

Effector cells were incubated 30 min with isotype control muIgG or chimeric A12 (muA12) diluted at 20 µg/ml and rabbit anti-mouse IgG (3 µ/test) before co-culture with target cells at different ratio (E/T: 10/1, 5/1, 2.5/1, 1/1). After 5 h of co-culture, cells were washed with PBS then stained with CD3-FITC, CD137-PE, CD107-APC and CD56-PC7. CD137 and CD107a expressions were analyzed on gated CD3− CD56+ cells Results:

Engagement of CD160-TM with an antibody of the present invention (muA12 antibody) enhances the expression of CD137 and the cell cytotoxicity (expression of CD107a) against K652 cells (FIGS. 7A-7B). Best results are obtained at low E/T ratio (1/1 and 2.5/1). Similar results were obtained with muB6 antibody (data not shown).

The invention claimed is:

1. A monoclonal antibody or an antigen binding fragment thereof, wherein said antibody or antigen binding fragment thereof comprises a light chain and a heavy chain, wherein the light chain comprises the following CDRs: i) VL-CDR1 as set forth in SEQ ID NO: 6 wherein $X_{11}$ is Y or S and $X_{12}$ is G or Y; ii) VL-CDR2 as set forth in SEQ ID NO: 7; and iii) VL-CDR3 as set forth in SEQ ID NO: 8 wherein $X_3$ is S or Y, and wherein the heavy chain comprises the following CDRs: i) VH-CDR1 as set forth in SEQ ID NO: 9 wherein $X_3$ is S or Y; ii) VH-CDR2 as set forth in SEQ ID NO: 10 wherein $X_1$ is Y or G and $X_{10}$ is N or S; and iii) the VH-CDR3 as set forth in SEQ ID NO: 11.

2. The monoclonal antibody or the antigen binding fragment thereof of claim 1, wherein said antibody or antigen binding fragment thereof comprises a light chain and a heavy chain, wherein the light chain comprises the following CDRs: i) VL-CDR1: AGTSSDVGGYYGVS (SEQ ID NO: 20); ii) VL-CDR2: YDSYRPS (SEQ ID NO: 7); and iii) VL-CDR3: SSSTYYSTRV (SEQ ID NO: 24), and wherein the heavy chain comprises the following CDRs: i) VH-CDR1: NYSMN (SEQ ID NO: 26); ii) VH-CDR2: YIYGSSRYISYADFVKG (SEQ ID NO: 29); and iii) VH-CDR3: GMDV (SEQ ID NO: 11).

3. The monoclonal antibody or the antigen binding fragment thereof of claim 1, wherein said antibody or antigen binding fragment thereof comprises a light chain and a heavy chain, wherein the light chain comprises the following CDRs: i) VL-CDR1: AGTSSDVGGYSYVS (SEQ ID NO: 23); ii) VL-CDR2: YDSYRPS (SEQ ID NO: 7); and iii) VL-CDR3: SSYTYYSTRV (SEQ ID NO: 25), and wherein the heavy chain comprises_the following CDRs: i) VH-CDR1: NYYMN (SEQ ID NO: 27); ii) VH-CDR2: GIYGSSRYINYADFVKG (SEQ ID NO: 30); and iii) VH-CDR3: GMDV (SEQ ID NO: 11).

4. The monoclonal antibody or the antigen binding fragment thereof of claim 1 comprising a heavy chain and a light chain, wherein the heavy chain has at least 95% of identity with SEQ ID NO: 12 or SEQ ID NO: 14 and wherein the light chain has at least 95% of identity with SEQ ID NO: 13 or SEQ ID NO: 15.

5. The monoclonal antibody or the antigen binding fragment of claim 1 comprising a heavy chain and a light chain wherein the heavy chain is identical to SEQ ID NO: 12 or SEQ ID NO: 14 and wherein the light chain is identical to SEQ ID NO: 13 or SEQ ID NO: 15.

6. A conjugated antibody comprising the monoclonal antibody or the antigen binding fragment thereof of claim 1 and a cytotoxic moiety.

7. A nucleic acid molecule which encodes a heavy chain or a light chain of the antibody or the antigen binding fragment thereof of claim 1.

8. The nucleic acid molecule of claim 7 which comprises a nucleic acid sequence identical to SEQ ID NO: 16, SEQ ID NO: 17, SEQ ID NO: 18 or SEQ ID NO: 19.

9. A method of activating natural killer (NK) cells in a human subject, comprising administering to the subject the monoclonal antibody or the antigen binding fragment thereof of claim 1, effective to activate NK cells.

10. The method of claim 9, wherein the subject has a cancer, and wherein the cancer is a gastrointestinal cancer, a skin cancer, a lung cancer, a stomach cancer, a colon cancer, a head cancer, a neck cancer, a kidney cancer, a liver cancer, or an esophagus cancer.

11. A fusion protein comprising the monoclonal antibody or the antigen binding fragment thereof of claim 1.

12. The monoclonal antibody or antigen binding fragment thereof of claim 1, which binds to the extracellular domain of the CD160-TM isoform, wherein said antibody or antigen binding fragment thereof does not bind to the GPI-anchored isoform nor to the CD160 soluble isoform, wherein the epitope of said monoclonal antibody or antigen binding fragment thereof comprises at least one amino acid residue from amino acid residues 175 to 189 of SEQ ID NO: 1, and wherein said epitope further comprises at least one amino acid residue from amino acid residues 62 to 85 of SEQ ID NO: 1.

13. The monoclonal antibody or antigen binding fragment thereof of claim 1, wherein the antibody or antigen binding fragment is chimeric, humanized or human.

14. The method of claim 9, wherein the subject has a disease or disorder selected from the group consisting of a cancer wherein the cancer cells do not express CD160-TM, an infectious disease, and an inflammatory disease.

* * * * *

SEQUENCE LISTING

```
<160> NUMBER OF SEQ ID NOS: 32

<210> SEQ ID NO 1
<211> LENGTH: 234
<212> TYPE: PRT
<213> ORGANISM: Artificial Sequence
<220> FEATURE:
<223> OTHER INFORMATION: CD160 transmembrane isoform
<300> PUBLICATION INFORMATION:
<301> AUTHORS: Giustiniani J., Bensussan A., Marie-Cardine A.
<302> TITLE: Identification and characterization of a transmembrane
      isoform of Identification and characterization of a transmembrane
``` isoform of CD160 (CD160-TM), a unique activating receptor selectively Identification and characterization of a transmembrane isoform of Ide
<303> JOURNAL: J Immunol
<304> VOLUME: 182
<305> ISSUE: 1
<306> PAGES: 63-71
<307> DATE: 2009
<300> PUBLICATION INFORMATION:
<310> PATENT DOCUMENT NUMBER: WO2008155363
<311> PATENT FILING DATE: 18/06/2008
<312> PUBLICATION DATE: 24/12/2008

<400> SEQUENCE: 1

```
Met Leu Leu Glu Pro Gly Arg Gly Cys Cys Ala Leu Ala Ile Leu Leu
1               5                   10                  15

Ala Ile Val Asp Ile Gln Ser Gly Gly Cys Ile Asn Ile Thr Ser Ser
            20                  25                  30

Ala Ser Gln Glu Gly Thr Arg Leu Asn Leu Ile Cys Thr Val Trp His
        35                  40                  45

Lys Lys Glu Glu Ala Glu Gly Phe Val Val Phe Leu Cys Lys Asp Arg
    50                  55                  60

Ser Gly Asp Cys Ser Pro Glu Thr Ser Leu Lys Gln Leu Arg Leu Lys
65                  70                  75                  80

Arg Asp Pro Gly Ile Asp Gly Val Gly Glu Ile Ser Ser Gln Leu Met
                85                  90                  95

Phe Thr Ile Ser Gln Val Thr Pro Leu His Ser Gly Thr Tyr Gln Cys
            100                 105                 110

Cys Ala Arg Ser Gln Lys Ser Gly Ile Arg Leu Gln Gly His Phe Phe
        115                 120                 125

Ser Ile Leu Phe Thr Glu Thr Gly Asn Tyr Thr Val Thr Gly Leu Lys
    130                 135                 140

Gln Arg Gln His Leu Glu Phe Ser His Asn Glu Gly Thr Leu Ser Ser
145                 150                 155                 160

Gly Phe Leu Gln Glu Lys Val Trp Val Met Leu Val Thr Ser Leu Val
                165                 170                 175

Ala Leu Gln Gly Met Ser Lys Arg Ala Val Ser Thr Pro Ser Asn Glu
            180                 185                 190

Gly Ala Ile Ile Phe Leu Pro Pro Trp Leu Phe Ser Arg Arg Arg Arg
        195                 200                 205

Leu Glu Arg Met Ser Arg Gly Arg Glu Lys Cys Tyr Ser Ser Pro Gly
    210                 215                 220

Tyr Pro Gln Glu Ser Ser Asn Gln Phe His
225                 230
```

<210> SEQ ID NO 2
<211> LENGTH: 160
<212> TYPE: PRT
<213> ORGANISM: Artificial Sequence
<220> FEATURE:
<223> OTHER INFORMATION: CD160 GPI-anchored isoform
<300> PUBLICATION INFORMATION:
<301> AUTHORS: Nikolova M., Marie-Cardine A., Boumsell L., Bensussan A.
<302> TITLE: BY55/CD160 acts as a co-receptor in TCR signal transduction of a BY55/CD160 acts as a co-receptor in TCR signal transduction of a human circulating cytotoxic effector T lymphocyte subset lacking BY55/CD160 acts as a co-receptor in TCR signal transduction of a
<303> JOURNAL: Int Immunol.
<304> VOLUME: 14
<305> ISSUE: 5
<306> PAGES: 445-51
<307> DATE: 2002

-continued

```
<300> PUBLICATION INFORMATION:
<310> PATENT DOCUMENT NUMBER: WO2006015886
<311> PATENT FILING DATE: 09/08/2005
<312> PUBLICATION DATE: 16/02/2006

<400> SEQUENCE: 2

Met Leu Leu Glu Pro Gly Arg Gly Cys Cys Ala Leu Ala Ile Leu Leu
1               5                   10                  15

Ala Ile Val Asp Ile Gln Ser Gly Gly Cys Ile Asn Ile Thr Ser Ser
            20                  25                  30

Ala Ser Gln Glu Gly Thr Arg Leu Asn Leu Ile Cys Thr Val Trp His
        35                  40                  45

Lys Lys Glu Glu Ala Glu Gly Phe Val Val Phe Leu Cys Lys Asp Arg
    50                  55                  60

Ser Gly Asp Cys Ser Pro Glu Thr Ser Leu Lys Gln Leu Arg Leu Lys
65                  70                  75                  80

Arg Asp Pro Gly Ile Asp Gly Val Gly Glu Ile Ser Ser Gln Leu Met
                85                  90                  95

Phe Thr Ile Ser Gln Val Thr Pro Leu His Ser Gly Thr Tyr Gln Cys
            100                 105                 110

Cys Ala Arg Ser Gln Lys Ser Gly Ile Arg Leu Gln Gly His Phe Phe
        115                 120                 125

Ser Ile Leu Phe Thr Glu Thr Gly Asn Tyr Thr Val Thr Gly Leu Lys
    130                 135                 140

Gln Arg Gln His Leu Glu Phe Ser His Asn Glu Gly Thr Leu Ser Ser
145                 150                 155                 160

<210> SEQ ID NO 3
<211> LENGTH: 160
<212> TYPE: PRT
<213> ORGANISM: Artificial Sequence
<220> FEATURE:
<223> OTHER INFORMATION: CD160 soluble isoform
<300> PUBLICATION INFORMATION:
<301> AUTHORS: Giustiniani J., Marie-Cardine A., Bensussan A.
<302> TITLE: A soluble form of the MHC class I-specific CD160 receptor
      is A soluble form of the MHC class I-specific CD160 receptor is
      released from human activated NK lymphocytes and inhibits A
      soluble form of the MHC class I-specific CD160 receptor is A
      soluble form of t
<303> JOURNAL: J Immunol.
<304> VOLUME: 178
<305> ISSUE: 3
<306> PAGES: 1293-300
<307> DATE: 2007

<400> SEQUENCE: 3

Met Leu Leu Glu Pro Gly Arg Gly Cys Cys Ala Leu Ala Ile Leu Leu
1               5                   10                  15

Ala Ile Val Asp Ile Gln Ser Gly Gly Cys Ile Asn Ile Thr Ser Ser
            20                  25                  30

Ala Ser Gln Glu Gly Thr Arg Leu Asn Leu Ile Cys Thr Val Trp His
        35                  40                  45

Lys Lys Glu Glu Ala Glu Gly Phe Val Val Phe Leu Cys Lys Asp Arg
    50                  55                  60

Ser Gly Asp Cys Ser Pro Glu Thr Ser Leu Lys Gln Leu Arg Leu Lys
65                  70                  75                  80

Arg Asp Pro Gly Ile Asp Gly Val Gly Glu Ile Ser Ser Gln Leu Met
                85                  90                  95

Phe Thr Ile Ser Gln Val Thr Pro Leu His Ser Gly Thr Tyr Gln Cys
            100                 105                 110
```

```
Cys Ala Arg Ser Gln Lys Ser Gly Ile Arg Leu Gln Gly His Phe Phe
        115                 120                 125

Ser Ile Leu Phe Thr Glu Thr Gly Asn Tyr Thr Val Thr Gly Leu Lys
    130                 135                 140

Gln Arg Gln His Leu Glu Phe Ser His Asn Glu Gly Thr Leu Ser Ser
145                 150                 155                 160

<210> SEQ ID NO 4
<211> LENGTH: 24
<212> TYPE: PRT
<213> ORGANISM: Artificial Sequence
<220> FEATURE:
<223> OTHER INFORMATION: Epitope

<400> SEQUENCE: 4

Lys Asp Arg Ser Gly Asp Cys Ser Pro Glu Thr Ser Leu Lys Gln Leu
1               5                   10                  15

Arg Leu Lys Arg Asp Pro Gly Ile
            20

<210> SEQ ID NO 5
<211> LENGTH: 15
<212> TYPE: PRT
<213> ORGANISM: Artificial Sequence
<220> FEATURE:
<223> OTHER INFORMATION: Epitope

<400> SEQUENCE: 5

Leu Val Ala Leu Gln Gly Met Ser Lys Arg Ala Val Ser Thr Pro
1               5                   10                  15

<210> SEQ ID NO 6
<211> LENGTH: 14
<212> TYPE: PRT
<213> ORGANISM: Artificial Sequence
<220> FEATURE:
<223> OTHER INFORMATION: VL-CDR1
<220> FEATURE:
<221> NAME/KEY: SITE
<222> LOCATION: 11
<223> OTHER INFORMATION: X is Y or S
<220> FEATURE:
<221> NAME/KEY: SITE
<222> LOCATION: 12
<223> OTHER INFORMATION: X is G or Y

<400> SEQUENCE: 6

Ala Gly Thr Ser Ser Asp Val Gly Gly Tyr Xaa Xaa Val Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: VL-CDR2

<400> SEQUENCE: 7

Tyr Asp Ser Tyr Arg Pro Ser
1               5

<210> SEQ ID NO 8
<211> LENGTH: 10
<212> TYPE: PRT
<213> ORGANISM: Artificial Sequence
<220> FEATURE:
```

```
<223> OTHER INFORMATION: VL-CDR3
<220> FEATURE:
<221> NAME/KEY: SITE
<222> LOCATION: 3
<223> OTHER INFORMATION: X is S or Y

<400> SEQUENCE: 8

Ser Ser Xaa Thr Tyr Tyr Ser Thr Arg Val
1               5                   10

<210> SEQ ID NO 9
<211> LENGTH: 5
<212> TYPE: PRT
<213> ORGANISM: Artificial Sequence
<220> FEATURE:
<223> OTHER INFORMATION: VH-CDR1
<220> FEATURE:
<221> NAME/KEY: SITE
<222> LOCATION: 3
<223> OTHER INFORMATION: X is S or Y

<400> SEQUENCE: 9

Asn Tyr Xaa Met Asn
1               5

<210> SEQ ID NO 10
<211> LENGTH: 17
<212> TYPE: PRT
<213> ORGANISM: Artificial Sequence
<220> FEATURE:
<221> NAME/KEY: SITE
<222> LOCATION: 1
<223> OTHER INFORMATION: X is Y or G
<220> FEATURE:
<223> OTHER INFORMATION: VH-CDR2
<220> FEATURE:
<221> NAME/KEY: SITE
<222> LOCATION: 10
<223> OTHER INFORMATION: X is N or S

<400> SEQUENCE: 10

Xaa Ile Tyr Gly Ser Ser Arg Tyr Ile Xaa Tyr Ala Asp Phe Val Lys
1               5                   10                  15
Gly

<210> SEQ ID NO 11
<211> LENGTH: 4
<212> TYPE: PRT
<213> ORGANISM: Artificial Sequence
<220> FEATURE:
<223> OTHER INFORMATION: VH-CDR3

<400> SEQUENCE: 11

Gly Met Asp Val
1

<210> SEQ ID NO 12
<211> LENGTH: 117
<212> TYPE: PRT
<213> ORGANISM: Artificial Sequence
<220> FEATURE:
<223> OTHER INFORMATION: VH region of A12 antibody

<400> SEQUENCE: 12

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30
```

Ser Met Asn Trp Val Arg Gln Ala Pro Gly Lys Gly Leu Glu Trp Ile
        35                  40                  45

Ser Tyr Ile Tyr Gly Ser Ser Arg Tyr Ile Ser Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Ser Tyr Tyr Gly Gly Met Asp Val Trp Gly Arg Gly Thr Leu
                100                 105                 110

Val Thr Val Ser Ser
            115

<210> SEQ ID NO 13
<211> LENGTH: 109
<212> TYPE: PRT
<213> ORGANISM: Artificial Sequence
<220> FEATURE:
<223> OTHER INFORMATION: VL region of A12 antibody

<400> SEQUENCE: 13

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
            20                  25                  30

Tyr Gly Val Ser Trp Tyr Gln Gln His Pro Gly Lys Ala Pro Lys Leu
        35                  40                  45

Met Ile Tyr Tyr Asp Ser Tyr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Ser Thr Tyr Tyr
                85                  90                  95

Ser Thr Arg Val Phe Gly Gly Gly Thr Lys Leu Glu Lys
                100                 105

<210> SEQ ID NO 14
<211> LENGTH: 117
<212> TYPE: PRT
<213> ORGANISM: Artificial Sequence
<220> FEATURE:
<223> OTHER INFORMATION: VH region of B6 antibody

<400> SEQUENCE: 14

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30

Tyr Met Asn Trp Val Arg Gln Ala Pro Gly Lys Gly Leu Glu Trp Ile
        35                  40                  45

Ser Gly Ile Tyr Gly Ser Ser Arg Tyr Ile Asn Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Ser Tyr Tyr Gly Gly Met Asp Val Trp Gly Arg Gly Thr Leu

```
                       100                 105                 110

Val Thr Val Ser Ser
            115

<210> SEQ ID NO 15
<211> LENGTH: 109
<212> TYPE: PRT
<213> ORGANISM: Artificial Sequence
<220> FEATURE:
<223> OTHER INFORMATION: VL region of B6 antibody

<400> SEQUENCE: 15

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
            20                  25                  30

Ser Tyr Val Ser Trp Tyr Gln Gln His Pro Gly Lys Ala Pro Lys Leu
        35                  40                  45

Met Ile Tyr Tyr Asp Ser Tyr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Tyr Tyr
                85                  90                  95

Ser Thr Arg Val Phe Gly Gly Gly Thr Lys Leu Glu Lys
            100                 105

<210> SEQ ID NO 16
<211> LENGTH: 345
<212> TYPE: DNA
<213> ORGANISM: Artificial Sequence
<220> FEATURE:
<223> OTHER INFORMATION: VH region of A12 antibody

<400> SEQUENCE: 16
aggtgcagct ggtggagtct gggggaagcc tggtcaagcc tgggggtcc  ctgagactct      60 cctgtgcagc tctggattca ccttcagtaa ctatagtatg aactgggtcc gccaggctcc     120
agggaagggc tggagtggat ctcatatatt tatggtagta gtagatatat aagttacgca     180
gacttcgtga aggcgattc  accatctcca gagacaacgc cacgaactca ctgtacctgc     240
aaatgaacag cctagagccg aggacacggc tgtttattac tgtgtgagat cctattatgg     300
cggtatggac gtctggggca gggcaccctg gtcaccgtct cctca                     345

<210> SEQ ID NO 17
<211> LENGTH: 325
<212> TYPE: DNA
<213> ORGANISM: Artificial Sequence
<220> FEATURE:
<223> OTHER INFORMATION: VL region of A12 antibody

<400> SEQUENCE: 17
cagtctgtgc tgactcagcc tgcctccgtg tctgggtctc ctggacagtc gatcaccatc      60
tcctgcgctg aaccagcagt gacgttggtg gttattatgg cgtctcctgg taccaacaac     120
acccaggaaa gccccaaac  tcatgattta ttatgacagt atcggcccct caggggtttc     180
taatcgcttc tctggcccaa gtctggcaac acggcctccc tgacaatctc tgggctccag     240
gctgaggacg aggcgattat tactgcagct caagtacata ttatagcact cgagttttcg     300
gcggagggac caagctggag ataaa                                           325
```

<210> SEQ ID NO 18
<211> LENGTH: 354
<212> TYPE: DNA
<213> ORGANISM: Artificial Sequence
<220> FEATURE:
<223> OTHER INFORMATION: VH region of B6 antibody

<400> SEQUENCE: 18

```
gaggtgcagc tggtggagtc tgggggaagc ctggtcaagc ctgggggtc  cctgagactc    60
tcctgtgcag cctctggatt caccttcagt aactattata tgaactgggt ccgccaggct   120
ccagggaagg gctggagtg atctcaggc atttatggta gtagtagata tataaactac    180
gcagacttcg tgaagggccg attcaccatc tccagagaca acgccacgaa ctcactgtac   240
ctgcaaatga acagcctgag agccgaggac acggctgttt attactgtgt gagatccagt   300
ggctatggcg gtatggacgt ctggggcaga ggcaccctgg tcaccgtctc ctca         354
```

<210> SEQ ID NO 19
<211> LENGTH: 330
<212> TYPE: DNA
<213> ORGANISM: Artificial Sequence
<220> FEATURE:
<223> OTHER INFORMATION: VL region of B6 antibody

<400> SEQUENCE: 19

```
cagtctgtgc tgactcagcc tgcctccgtg tctgggtctc ctggacagtc gatcaccatc    60
tcctgcgctg gaaccagcag tgacgttggt ggttatagtt atgtctcctg gtaccaacaa   120
cacccaggca aagcccccaa actcatgatt tattatgaca gttatcggcc ctcagggtt    180
tctaatcgct tctctggctc caagtctggc aacacggcct ccctgacaat ctctgggctc   240
caggctgagg acgaggctga ttattactgc agctcatata catattatag cactcgagtt   300
ttcggcggag ggaccaagct ggagatcaaa                                    330
```

<210> SEQ ID NO 20
<211> LENGTH: 14
<212> TYPE: PRT
<213> ORGANISM: Artificial Sequence
<220> FEATURE:
<223> OTHER INFORMATION: VL-CDR1

<400> SEQUENCE: 20

Ala Gly Thr Ser Ser Asp Val Gly Gly Tyr Tyr Gly Val Ser
1               5                   10

<210> SEQ ID NO 21
<211> LENGTH: 14
<212> TYPE: PRT
<213> ORGANISM: Artificial Sequence
<220> FEATURE:
<223> OTHER INFORMATION: VL-CDR1

<400> SEQUENCE: 21

Ala Gly Thr Ser Ser Asp Val Gly Gly Tyr Tyr Tyr Val Ser
1               5                   10

<210> SEQ ID NO 22
<211> LENGTH: 14
<212> TYPE: PRT
<213> ORGANISM: Artificial Sequence
<220> FEATURE:
<223> OTHER INFORMATION: VL-CDR1

<400> SEQUENCE: 22

Ala Gly Thr Ser Ser Asp Val Gly Gly Tyr Ser Gly Val Ser
1               5                   10

<210> SEQ ID NO 23
<211> LENGTH: 14
<212> TYPE: PRT
<213> ORGANISM: Artificial Sequence
<220> FEATURE:
<223> OTHER INFORMATION: VL-CDR1

<400> SEQUENCE: 23

Ala Gly Thr Ser Ser Asp Val Gly Gly Tyr Ser Tyr Val Ser
1               5                   10

<210> SEQ ID NO 24
<211> LENGTH: 10
<212> TYPE: PRT
<213> ORGANISM: Artificial Sequence
<220> FEATURE:
<223> OTHER INFORMATION: VL-CDR3

<400> SEQUENCE: 24

Ser Ser Ser Thr Tyr Tyr Ser Thr Arg Val
1               5                   10

<210> SEQ ID NO 25
<211> LENGTH: 10
<212> TYPE: PRT
<213> ORGANISM: Artificial Sequence
<220> FEATURE:
<223> OTHER INFORMATION: VL-CDR3

<400> SEQUENCE: 25

Ser Ser Tyr Thr Tyr Tyr Ser Thr Arg Val
1               5                   10

<210> SEQ ID NO 26
<211> LENGTH: 5
<212> TYPE: PRT
<213> ORGANISM: Artificial Sequence
<220> FEATURE:
<223> OTHER INFORMATION: VH-CDR1

<400> SEQUENCE: 26

Asn Tyr Ser Met Asn
1               5

<210> SEQ ID NO 27
<211> LENGTH: 5
<212> TYPE: PRT
<213> ORGANISM: Artificial Sequence
<220> FEATURE:
<223> OTHER INFORMATION: VH-CDR1

<400> SEQUENCE: 27

Asn Tyr Tyr Met Asn
1               5

<210> SEQ ID NO 28
<211> LENGTH: 17
<212> TYPE: PRT
<213> ORGANISM: Artificial Sequence
<220> FEATURE:
<223> OTHER INFORMATION: VH-CDR2

<400> SEQUENCE: 28

```
Tyr Ile Tyr Gly Ser Ser Arg Tyr Ile Asn Tyr Ala Asp Phe Val Lys
1               5                   10                  15

Gly

<210> SEQ ID NO 29
<211> LENGTH: 17
<212> TYPE: PRT
<213> ORGANISM: Artificial Sequence
<220> FEATURE:
<223> OTHER INFORMATION: VH-CDR2

<400> SEQUENCE: 29

Tyr Ile Tyr Gly Ser Ser Arg Tyr Ile Ser Tyr Ala Asp Phe Val Lys
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: VH-CDR2

<400> SEQUENCE: 30

Gly Ile Tyr Gly Ser Ser Arg Tyr Ile Asn Tyr Ala Asp Phe Val Lys
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: VH-CDR2

<400> SEQUENCE: 31

Gly Ile Tyr Gly Ser Ser Arg Tyr Ile Ser Tyr Ala Asp Phe Val Lys
1               5                   10                  15

Gly

<210> SEQ ID NO 32
<211> LENGTH: 16
<212> TYPE: PRT
<213> ORGANISM: Artificial Sequence
<220> FEATURE:
<223> OTHER INFORMATION: Peptide 2 - amino acids 144-158 of CD160-TM
<300> PUBLICATION INFORMATION:
<310> PATENT DOCUMENT NUMBER: WO2008155363
<311> PATENT FILING DATE: 18/06/2008
<312> PUBLICATION DATE: 24/12/2008

<400> SEQUENCE: 32

Lys Gln Arg Gln His Leu Glu Phe Ser His Asn Asn Glu Gly Thr Leu
1               5                   10                  15
```